US012089949B2

(12) United States Patent
Fox et al.

(10) Patent No.: US 12,089,949 B2
(45) Date of Patent: Sep. 17, 2024

(54) SLEEP STATUS DETECTION FOR APNEA-HYPOPNEA INDEX CALCULATION

(71) Applicant: ResMed Sensor Technologies Limited, Dublin (IE)

(72) Inventors: Niall Fox, Dublin (IE); Anna Rice, Dublin (IE); Stephen McMahon, Dublin (IE); Graeme Lyon, Dublin (IE); Redmond Shouldice, Dublin (IE); Stephen Dodd, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 89 days.

(21) Appl. No.: 17/796,675

(22) PCT Filed: Jan. 31, 2021

(86) PCT No.: PCT/IB2021/050755
§ 371 (c)(1),
(2) Date: Jul. 31, 2022

(87) PCT Pub. No.: WO2021/152551
PCT Pub. Date: Aug. 5, 2021

(65) Prior Publication Data
US 2023/0099622 A1     Mar. 30, 2023

Related U.S. Application Data

(60) Provisional application No. 63/002,585, filed on Mar. 31, 2020, provisional application No. 62/968,775, filed on Jan. 31, 2020.

(51) Int. Cl.
*A61B 5/00*      (2006.01)

(52) U.S. Cl.
CPC .......... *A61B 5/4818* (2013.01); *A61B 5/4809* (2013.01); *A61B 5/4812* (2013.01)

(58) Field of Classification Search
CPC ... A61B 5/4806; A61B 5/4809; A61B 5/4812; A61B 5/4815; A61B 5/4818
See application file for complete search history.

(56) References Cited

U.S. PATENT DOCUMENTS

| 10,278,639 B2 | 5/2019 | Alshaer et al. |
| 2014/0008837 A1 | 1/2014 | Eatherton |

(Continued)

FOREIGN PATENT DOCUMENTS

| WO | 2007/143535 A2 | 12/2007 |
| WO | 2010/091362 A2 | 8/2010 |

(Continued)

OTHER PUBLICATIONS

International Search Report in International Patent Application No. PCT/IB2021/050755 mailed Jun. 28, 2021 (6 pp.).

(Continued)

*Primary Examiner* — Benyam Haile
(74) *Attorney, Agent, or Firm* — NIXON PEABODY LLP

(57) ABSTRACT

Devices, systems, and methods are disclosed. The devices, systems, and methods detect one or more parameters with respect to movement of a user, cardiac activity of the user, audio associated with the user, or a combination thereof during a sleep session of the user; process the one or more parameters to determine a sleep status of the user, the sleep status being at least one of awake, asleep, or a sleep stage; and calculate an apnea-hypopnea index for the user during the sleep session based, at least in part, on the sleep status.

28 Claims, 6 Drawing Sheets

(56) References Cited

U.S. PATENT DOCUMENTS

| | | | |
|---|---|---|---|
| 2015/0164375 A1* | 6/2015 | Schindhelm | A61B 5/113 600/534 |
| 2015/0164409 A1* | 6/2015 | Benson | A61B 5/1116 600/595 |
| 2017/0312117 A1* | 11/2017 | Shah | A61B 5/01 |
| 2019/0000375 A1 | 1/2019 | Ferreira Dos Santos Da Fonseca et al. | |

FOREIGN PATENT DOCUMENTS

| | | |
|---|---|---|
| WO | 2012/012835 A2 | 2/2012 |
| WO | 2014/047110 A2 | 3/2014 |
| WO | 2015/006164 A2 | 1/2015 |
| WO | 2016/061629 A1 | 4/2016 |
| WO | 2017/132726 A1 | 8/2017 |
| WO | 2018/050913 A1 | 3/2018 |
| WO | 2019/122412 A1 | 6/2019 |
| WO | 2019/122413 A1 | 6/2019 |
| WO | 2019/122414 A1 | 6/2019 |
| WO | 2020/104465 A2 | 5/2020 |

OTHER PUBLICATIONS

Written Opinion in International Patent Application No. PCT/IB2021/050755 mailed Jun. 28, 2021 (12 pp.).

* cited by examiner

SLEEP STATUS DETECTION FOR APNEA-HYPOPNEA INDEX CALCULATION

CROSS-REFERENCE TO RELATED APPLICATIONS

The present application is a U.S. National Stage of International Application No. PCT/IB2021/050755, filed on Jan. 31, 2021, which claims the benefit of and priority to U.S. Provisional Patent Application No. 63/002,585, filed on Mar. 31, 2020, and entitled, "SLEEP STATUS DETECTION FOR APNEA-HYPOPNEA INDEX CALCULATION," and U.S. Provisional Patent Application No. 62/968,775, filed on Jan. 31, 2020, and entitled, "SLEEP STATUS DETECTION FOR APNEA-HYPOPNEA INDEX CALCULATION," the contents of which are hereby incorporated by reference herein in their entireties.

FIELD OF THE TECHNOLOGY

The present technology relates to devices, systems, and methods for sleep status detection, and determination of an Apnea Hypopnea Index (AHI) that takes into account the sleep status.

BACKGROUND OF THE TECHNOLOGY

Whether a user is asleep or awake can be considered a sleep state. Once asleep, sleep can be characterized by four distinct sleep stages that change throughout the night. A user, and particularly a healthy user, moves between the sleep stages, usually in an order, a number of times during sleep. The sleep stages include N1, N2, and N3, known together as non-REM stages, and REM.

Stage N1 is the lightest sleep stage and is characterized by the appearance of some low amplitude waves at multiple frequencies interspersed with the alpha waves for greater than 50% of an epoch. There may also be sharp vertex waves, some slow eye movements on electrooculography (EOG) signals, and/or an overall lowering of the frequency of electroencephalogram (EEG) signals.

Stage N2 is a slightly deeper sleep stage and is marked by the appearance of sleep spindles and K-complexes, on a background of mixed frequency signals. Sleep spindles are bursts of higher frequency activity (e.g., greater than 12 Hz). K-complexes are distinct isolated bipolar waves lasting about 1-2 seconds.

Stage N3 is the deepest sleep stage and is characterized by the appearance of slow waves (e.g., 1-2 Hz frequency) for at least 20% of an epoch.

Stage REM is rapid eye movement sleep and is apparent through the presence of distinct activity in the EOG signal. The EEG signals recorded are typically quite similar to Stage N1 or even awake.

The term sleep-disordered breathing (SDB) can refer to conditions where apneas (e.g., cessation of airflow for ten seconds or more) and hypopneas (e.g., decrease in airflow that is at least 30% for 10 seconds or more with an associated oxygen desaturation or arousal) are present during sleep.

Breathing instability is an indicator of wakefulness or REM sleep, and breathing stability is an indicator of non-REM (e.g., N1, N2, N3) sleep. Breathing instability alone, however, is insufficient to infer sleep stage accurately. For example, breathing instability is an indicator of wakefulness or REM sleep, it can also occur as a result of frequent respiratory events, such as apneas, hypopneas, and respiratory effort-related arousals (RERAs), which occur during sleep. It is therefore helpful to distinguish periods of breathing instability that are largely driven by respiratory events from periods of genuine wakefulness.

While positive airway pressure respiratory devices can be configured to detect sleep-disordered breathing (SDB) events, such as apneas and hypopneas, in real time, they often miss-detect SDB events based on the user not being asleep or the user being in the incorrect stage of sleep. For example, analysis of flow can lead to determinations as to whether a user is asleep, and even what stage of sleep. However, there are limitations on such flow-based sleep staging. It can be difficult to accurately distinguish between awake and sleep states with flow-based signals. Flow-based signals can be fragmented, missing information at the beginning, the middle (when go to rest room or take off in middle of night), and the end.

It is of interest to know when the user went to sleep, when the user awoke, and what stages of sleep the user passed through in the meantime. A complete representation of the various sleep stages passed through by a user during a sleep session is called a hypnogram. One example application of a hypnogram is the computation of an index of severity of SDB known as the apnea-hypopnea index (AHI). AHI, which is usually calculated as the total number of apneas and hypopneas divided by the length of the sleep session, is a widely-used screening, diagnostic, and monitoring tool for SDB. However, such calculation tends to underestimate the AHI, since for significant periods during the session the user may not have been asleep. The result is that a user tends to get an overly optimistic picture of the efficacy of the user's therapy if conventional AHI calculation is employed. With respect to, flow-based sleep staging in particular, it is biased toward sleep so SDB events that occur during awake are counted incorrectly into the AHI. Conversely, the AHI may be over-estimated if SDB events are detected in error when the user is awake and moving. Over and/or under estimating could mean that, for example, an autoset algorithm of a respiratory device adapts therapy in a way that negatively impacts sleep quality and/or efficacy of therapy.

A more accurate method of calculating the AHI is to divide the number of apneas and hypopneas by the number of hours the user was asleep during the session. To compute the AHI in this way requires knowledge of when the user was asleep, knowledge which may be obtained from a hypnogram. However, inferring sleep stage purely from respiratory flow rate has proven to be a difficult task, with consequent effects on the accuracy of AHI calculation and hence AHI-based monitoring of users on respiratory therapy (e.g. continuous positive airway pressure (CPAP) therapy).

A need therefore exists to develop improved devices, systems, and methods for inferring states and stages of a respiratory therapy user's sleep in order to more accurately assess the user's condition and the efficacy of the applied therapy, which can improve sleep architecture by treating SDB.

SUMMARY

According to some aspects of the present disclosure, devices, systems, and methods for distinguishing respiratory event sleep from wakefulness based on a sleep status are disclosed.

According to some aspects of the present disclosure, devices, systems, and methods are disclosed that detect sleep and provide feedback to a user concerning a sleep status.

According to one implementation of the present disclosure, disclosed is a method for detecting a sleep status of a user. The method includes detecting one or more parameters with respect to movement of a user during a sleep session of the user. The method further includes processing the one or more parameters to determine a sleep status of the user. The sleep status is at least one of awake, asleep, or a sleep stage. The method further includes calculating an apnea-hypopnea index for the user during the sleep session based, at least in part, on the sleep status.

According to some aspects of the implementation, the sleep stage can be an indication of non-REM sleep, N1 sleep, N2, sleep, N3 sleep, or REM sleep. According to some aspects of the implementation, the one or more events that affect the calculation of the apnea-hypopnea index of the user are disregarded in response to the sleep status being determined as awake during the one or more events. Further, the one or more events are one or more apneas, one or more hypopneas, or a combination thereof. According to some aspects of the implementation, the one or more parameters relate to duration, frequency, intensity, type of movement of the user, or a combination thereof. According to some aspects of the implementation, the one or more parameters are measured based on one or more sensors placed on the user, placed in proximity of the user, or a combination thereof. Pressurized air can be applied to an airway of the user through a tube and a mask connected to a respiratory device. At least one sensor of the one or more sensors can be on or within the tube, the mask, or a combination thereof. The at least one sensor can include an inertial measurement unit on or within the tube, the mask, or a combination thereof. At least one sensor of the one or more sensors can include an inertial measurement unit within a smart device coupled to the user. The smart device can be one or more of (1) a smart watch, a smart phone, an activity tracker, a smart mask, a smart garment, a smart mattress, a smart pillow, smart sheets, a smart ring, or a health monitor, each one being in contact with the user, (2) a smart speaker or a smart TV, each one being in proximity of the user, (3) or a combination thereof. According to some aspects of the implementation, the processing of the one or more parameters includes processing a signal representative of at least one parameter of the one or more parameters over time.

According to another implementation of the present disclosure, disclosed is a method for detecting a sleep state of a user. The method includes detecting one or more parameters with respect to cardiac activity of a user during a sleep session of the user, which can include applying pressurized air to an airway of the user. The method further includes processing the one or more parameters to determine a sleep status of the user. The sleep status is at least one of awake, asleep, or a sleep stage. The method further includes calculating an apnea-hypopnea index for the user during the sleep session based, at least in part, on the sleep status.

According to some aspects of the implementation, one or more events that affect the calculating of the apnea-hypopnea index of the user are disregarded in response to the sleep status being determined as awake during the one or more events. The one or more events are one or more apneas, one or more hypopneas, or a combination thereof. According to some aspects of the implementation, the one or more parameters relate to heart rate, heart rate variability, cardiac output, or a combination thereof of the user. The heart rate variability can be calculated over a period of time of one minute, five minutes, ten minutes, half an hour, an hour, two hours, three hours, or four hours. According to some aspects of the implementation, the pressurized air can be applied to the airway of the user through a tube and a mask connected to a respiratory device, and at least one sensor of the one or more parameters can be on or within the tube, the mask, or a combination thereof. In one or more implementations, the at least one sensor can be a microphone. The detecting of the one or more parameters can be based on a cepstrum analysis, a spectral analysis, a fast Fourier transform, or a combination thereof of one or more flow signals, one or more audio signals, or a combination thereof.

According to one implementation of the present disclosure, disclosed is a method for detecting a sleep status of a user. The method includes detecting one or more parameters with respect to audio associated with a user during a sleep session of the user, which can include applying pressurized air to an airway of the user. The method further includes processing the one or more parameters to determine a sleep status of the user. The sleep status is at least one of awake, asleep, or a sleep stage. The method further includes calculating an apnea-hypopnea index for the user during the sleep session based, at least in part, on the sleep status.

According to some aspects of the implementation, one or more events that affect the calculating of the apnea-hypopnea index of the user are disregarded in response to the sleep status being determined as awake during the one or more events. The one or more events are one or more apneas, one or more hypopneas, or a combination thereof. According to some aspects of the implementation, the audio is associated with (1) one or more movements of the user, (2) one or more movements of a tube, a mask, or a combination thereof connected to a respiratory device configured to apply the pressurized air to the user, or (3) a combination thereof. The detecting of the one or more parameters with respect to audio associated with the one or more movements of the tube, the mask, or a combination thereof can be based on a cepstrum analysis, a spectral analysis, a fast Fourier transform, or a combination thereof of one or more flow signals, one or more audio signals, or a combination thereof. According to some aspects of the implementation, the audio can be detected based on one or more microphones within a tube, a mask, or an apparatus connected to the tube and the apparatus and that provides the pressurized air to the airway of the user.

According to one implementation of the present disclose, a method for detecting a sleep status of a user is disclosed. The method includes detecting a plurality of parameters associated with an individual during a sleep session or a user during a session of applying pressurized air to an airway of the user, wherein each parameter of the plurality of parameters is associated at least with one modality, and the plurality of parameters cover a plurality of modalities. The method further includes processing the plurality of parameters to determine a sleep status of the user, the sleep status being at least one of awake, asleep, or a sleep stage. The method further includes calculating an apnea-hypopnea index for the user during the session based, at least in part, on the sleep status. Moreover, multiple modalities can be combined, where one or more modalities associated with or determined from a respiratory therapy system 120 are not used. For example, sleep status and/or stage can be determined, in combination with AHI from the modality related to cardiac activity. Thereafter, one or more other parameters related to movement, and which are unrelated to cardiac activity, can be used to confirm the sleep status and/or stage based on cardiac activity. As a further example, AHI (but not necessarily sleep state and/or stage) can be determined from blood oxygen levels, or some other parameter(s) that cannot capture sleep stage and/or stage. Thereafter, another parameter related to a different modality, such as movement, cardiac activity, etc., can be used to confirm the sleep state and/or stage.

According to some aspects of the implementation, the modalities include two or more of movement of the user, flow of the pressurized air, cardiac activity of the user, and audio associated with the user. According to some aspects of the implementation, one or more events that affect the calculating of the apnea-hypopnea index of the user are disregarded in response to the sleep status being determined as awake during the one or more events. The one or more events include one or more apneas, one or more hypopneas, or a combination thereof. According to some aspects of the implementation, the processing of the plurality of parameters further includes determining that the sleep status of the user cannot be determined based on one or more parameters of the plurality of parameters associated with a first modality of the two or more modalities. The processing of the plurality of parameters the further includes processing one or more parameters of the plurality of parameters associated with a second modality of the two or more modalities to determine the sleep status of the user. According to some aspects of the implementation, the determination that the sleep status of the user cannot be determined is based on satisfaction of a threshold determination metric. The threshold determination metric can be based on two or more parameters of the plurality of parameters conflicting with respect to sleep status, sleep status, or a combination thereof. The two or more conflicting parameters are from the two or more modalities. A conflict between two or more conflicting parameters is resolved by disregarding a parameter derived on a basis of low quality data and/or increased weight is given to a parameter extracted from data of higher quality. The threshold determination metric can be based on a plurality of previous parameters associated with the user during one or more previous sessions of applying pressurized air to the airway of the user. According to some aspects of the implementation, the processing is performed by a sleep staging classifier based on one or more of supervised machine learning, deep learning, a convolutional neural network, or a recurrent neural network. According to some aspects, the processing of the plurality of parameters is based on a sub-set of the plurality of parameters from a selected two or more modalities of the plurality of modalities. The selected two or more modalities can be selected in accordance with a weighting based on data quality.

According to one or more implementations, one or more systems are disclosed that can include one or more sensors that are configured to detect one or more parameters disclosed herein, a respiratory device having a tube and a mask coupled to a user; memory storing machine-readable instructions; and a control system including one or more processors configured to execute the machine-readable instructions to perform the methods disclosed herein.

Some versions of the present technology may include a computer processor-readable memory storage apparatus having processor-executable instructions encoded thereon which, when executed by a processor, cause the processor to perform any one or more of the methods disclosed herein.

According to one implementation of the present disclosure, disclosed is a method for calculating an apnea-hypopnea index of a user. The method includes detecting one or more parameters with respect to movement of a user during a sleep session of the user, which can include applying pressurized air to an airway of the user. The method further includes processing the one or more parameters to determine a sleep status of the user. The sleep status can be at least one of awake, asleep or a sleep stage. The method further includes calculating the apnea-hypopnea index for the user during the sleep session based, at least in part, on the sleep status. The method further includes initiating an action based, at least in part, on the apnea-hypopnea index, the sleep status, or a combination thereof.

According to some aspects of the implementation, the action includes one or more of (1) saving a record of the apnea-hypopnea index, (b) communicating the apnea-hypopnea index to an external device, or (c) adjusting an operational setting of a device. The device can be a respiratory device supplying the pressured air to the airway of the user. According to some aspects of the implementation, one or more events that affect the calculating of the apnea-hypopnea index of the user are disregarded in response to the sleep status being determined as awake during the one or more events. The one or more events can be one or more apneas, one or more hypopneas, one or more periodic limb movements, or a combination thereof. According to some aspects of the implementation, the one or more parameters can relate to duration, period, rate, frequency, intensity, type of movement of the user, or a combination thereof. According to some aspects of the implementation, the one or more parameters can be measured based on one or more sensors placed on the user, placed in proximity of the user, or a combination thereof. The pressurized air can be applied to the airway of the user through a tube and a mask connected to a respiratory device, and at least one sensor of the one or more sensors is on or within the tube, on or within the mask, or a combination thereof. The at least one sensor can include a physical motion sensor on or within the tube, on or within the mask, or a combination thereof. According to some aspects of the implementation, at least one sensor of the one or more sensors includes a physical motion sensor within a smart device. The smart device can be one or more of (1) a smart watch, a smart phone, an activity tracker, a smart mask, a smart garment, a smart mattress, a smart pillow, smart sheets, a smart ring, or a health monitor, each one being in contact with the user, (2) a smart speaker or a smart TV, each one being in proximity of the user, (3) or a combination thereof. According to some aspects of the implementation, the processing of the one or more parameters includes processing a signal representative of at least one parameter of the one or more parameters over time. According to some aspects of the implementation, the movement of the user can be associated with cardiac or respiratory activity of the user. The at least one sensor can be a microphone. The detecting of the one or more parameters can be based on a cepstrum analysis, a spectral analysis, a fast Fourier transform, or a combination thereof of one or more flow signals, one or more audio signals, or a combination thereof. According to some implementations, the detection of the one or more parameters can be with respect to audio associated with a user during the session. The audio can be associated with (1) one or more movements of the user, (2) one or more movements of a tube, a mask, or a combination thereof connected to a respiratory device configured to apply the pressurized air to the user, or (3) a combination thereof. The detecting of the one or more parameters with respect to the audio can be based on a cepstrum analysis, a spectral analysis, a fast Fourier transform, or a combination thereof of one or more flow signals, one or more audio signals, or a combination thereof. The audio can be detected based on one or more microphones within a tube, a mask, or an apparatus connected to the tube and the apparatus and that provides the pressurized air to the airway of the user. According to some implementations, each parameter of the one or more plurality of parameters can be associated at least with one modality, and a plurality of the one or more parameters cover a plurality of modalities. The modalities can include movement of the user, flow of the pressurized air, cardiac activity of the user, and audio associated with the user. The processing of the plurality of parameters can further include determining that the sleep status of the user cannot be determined based on one or more parameters of the plurality of parameters associated with a first modality of the two or more modalities; and processing one or more parameters of the plurality of parameters associated with a second modality of the two or more modalities to determine the sleep status of the user. According to some aspects of the implementation, the determination that the sleep status of the user cannot be determined can be based on satisfaction of a threshold determination metric. The threshold determination metric can be based on two or more parameters of the plurality of parameters conflicting with respect to the determined sleep status, sleep stage, or a combination thereof. The two or more conflicting parameters are from the two or more modalities. A conflict between two or more conflicting parameters can be resolved by disregarding a parameter derived on a basis of low quality data and/or increased weight is given to a parameter extracted from data of higher quality. According to some aspects of the implementation, the threshold determination metric can be based on a plurality of previous parameters associated with the user during one or more previous sessions of applying pressurized air to the airway of the user. According to some aspects of the implementation, the processing can be performed by a sleep staging classifier based on one or more of supervised machine learning, deep learning, a convolutional neural network, or a recurrent neural network.

According to one implementation of the present disclosure, disclosed is system for calculating an apnea-hypopnea index of a user. The system includes one or more sensors configured to detect one or more parameters with respect to movement of a user during a sleep session of the user, which can include a session of applying pressurized air to an airway of the user. The system further includes memory storing machine-readable instructions and a control system. The control system includes one or more processors configured to execute the machine-readable instructions to: process the one or more parameters to determine a sleep status of the user, the sleep status being at least one of awake, asleep or a sleep stage; calculate the apnea-hypopnea index for the user during the sleep session based, at least in part, on the sleep status; and initiate an action based, at least in part, on the apnea-hypopnea index, the sleep status, or a combination thereof.

According to some aspects of the implementation, the action includes one or more of (1) saving a record of the apnea-hypopnea index, (b) communicating the apnea-hypopnea index to an external device, or (c) adjusting an operational setting of a device. The device is a respiratory device supplying the pressured air to the airway of the user. According to some aspects of the implementation, one or more events that affect the calculating of the apnea-hypopnea index of the user are disregarded in response to the sleep status being determined as awake during the one or more events. The one or more events are one or more apneas, one or more hypopneas, one or more periodic limb movements, or a combination thereof. According to some aspects of the implementation, the one or more parameters relate to duration, period, rate, frequency, intensity, type of movement of the user, or a combination thereof. According to some aspects of the implementation, the one or more sensors are placed on the user, placed in proximity of the user, or a combination thereof. According to some aspects of the implementation, the system further includes a respiratory device having a tube and a mask coupled to the user. The pressurized air can be applied to the airway of the user through the tube and the mask, and at least one sensor of the one or more sensors is on or within the tube, the mask, or a combination thereof. The one or more sensors can include a physical motion sensor on or within the tube, the mask, or a combination thereof. According to some aspects of the implementation, at least one sensor of the one or more sensors can include a physical motion sensor within a smart device. The smart device can be one or more of (1) a smart watch, a smart phone, an activity tracker, a smart mask, a smart garment, a smart mattress, a smart pillow, smart sheets, a smart ring, or a health monitor, each one being in contact with the user, (2) a smart speaker or a smart TV, each one being in proximity of the user, (3) or a combination thereof. According to some aspects of the implementation, the processing of the one or more parameters can include processing a signal representative of at least one parameter of the one or more parameters over time. According to some aspects of the implementation, the movement of the user can be associated with cardiac or respiratory activity of the user. The at least one sensor can be a microphone. The detecting of the one or more parameters can be based on a cepstrum analysis, a spectral analysis, a fast Fourier transform, or a combination thereof of one or more flow signals, one or more audio signals, or a combination thereof detected by the microphone. According to some aspects of the implementation, the detection of the one or more parameters can be with respect to audio associated with a user during the sleep session. According to some aspects of the implementation, the audio can be associated with (1) one or more movements of the user, (2) one or more movements of a tube, a mask, or a combination thereof connected to a respiratory device configured to apply the pressurized air to the user, or (3) a combination thereof. According to some aspects of the implementation, the detecting of the one or more parameters with respect to the audio can be based on a cepstrum analysis, a spectral analysis, a fast Fourier transform, or a combination thereof of one or more flow signals, one or more audio signals, or a combination thereof. According to some aspects of the implementation, the audio can be detected based on one or more microphones within a tube, a mask, or an apparatus connected to the tube and the apparatus and that provides the pressurized air to the airway of the user. According to some aspects of the implementation, each parameter of the one or more parameters is associated at least with one modality, and the one or more parameters cover a plurality of modalities. The modalities can include movement of the user, flow of the pressurized air, cardiac activity of the user, and audio associated with the user. The control system can be configured to execute the machine-readable instructions to determine that the sleep status of the user cannot be determined based on one or more parameters of the plurality of parameters associated with a first modality of the two or more modalities; and process one or more parameters of the plurality of parameters associated with a second modality of the two or more modalities to determine the sleep status of the user. According to some aspects of the implementation, the determination that the sleep status of the user cannot be determined is based on satisfaction of a threshold determination metric. The threshold determination metric can be based on two or more parameters of the plurality of parameters conflicting with respect to the determined sleep status, sleep stage, or a combination thereof. The two or more conflicting parameters can be from the two or more modalities. According to some aspects of the implementation, a conflict between two or more conflicting parameters can be resolved by disregarding a parameter derived on a basis of low quality data and/or increased weight is given to a parameter extracted from data of higher quality. According to some aspects of the implementation, the threshold determination metric can be based on a plurality of previous parameters associated with the user during one or more previous sessions of applying pressurized air to the airway of the user. According to some aspects of the implementation, the processing can be performed by a sleep staging classifier based on one or more of supervised machine learning, deep learning, a convolutional neural network, or a recurrent neural network. According to some aspects of the implementation, each parameter of the one or more parameters can be associated at least with one modality, and the one or more parameters cover a plurality of modalities. The processing of the plurality of parameters can be based on a sub-set of the plurality of parameters from a selected two or more modalities of the plurality of modalities. The selected two or more modalities can be selected in accordance with a weighting based on data quality. According to some aspects of the implementation, the sleep stage can be an indication of non-REM sleep or REM sleep. According to some aspects of the implementation, the sleep stage can be an indication of N1 sleep, N2, sleep, N3 sleep, or REM sleep.

According to one implementation of the present disclosure, a system is disclosed that includes a control system having one or more processors. The system further incudes a memory having stored thereon machine readable instructions. The control system is coupled to the memory, and any one or more of the methods disclosed above is implemented when the machine executable instructions in the memory are executed by at least one of the one or more processors of the control system.

According to one implementation of the present disclosure, a system is disclosed that includes a control system configured to implement any one or more of the methods disclosed above.

According to one implementation of the present disclosure, a computer program product is disclosed that includes instructions that, when executed by a computer, cause the computer to carry out any one or more of the methods disclosed above. In one or more implementations, the computer program product is a non-transitory computer readable medium.

Portions of the above aspects may form sub-aspects of the present technology. Other features of the technology will be apparent from consideration of the information contained in the following detailed description, abstract, drawings and claims. Also, various ones of the sub-aspects and/or aspects may be combined in various manners and also constitute additional aspects or sub-aspects of the present technology. The above summary is not intended to represent each implementation or every aspect of the present disclosure. Additional features and benefits of the present disclosure are apparent from the detailed description and figures set forth below.

Figure 1:
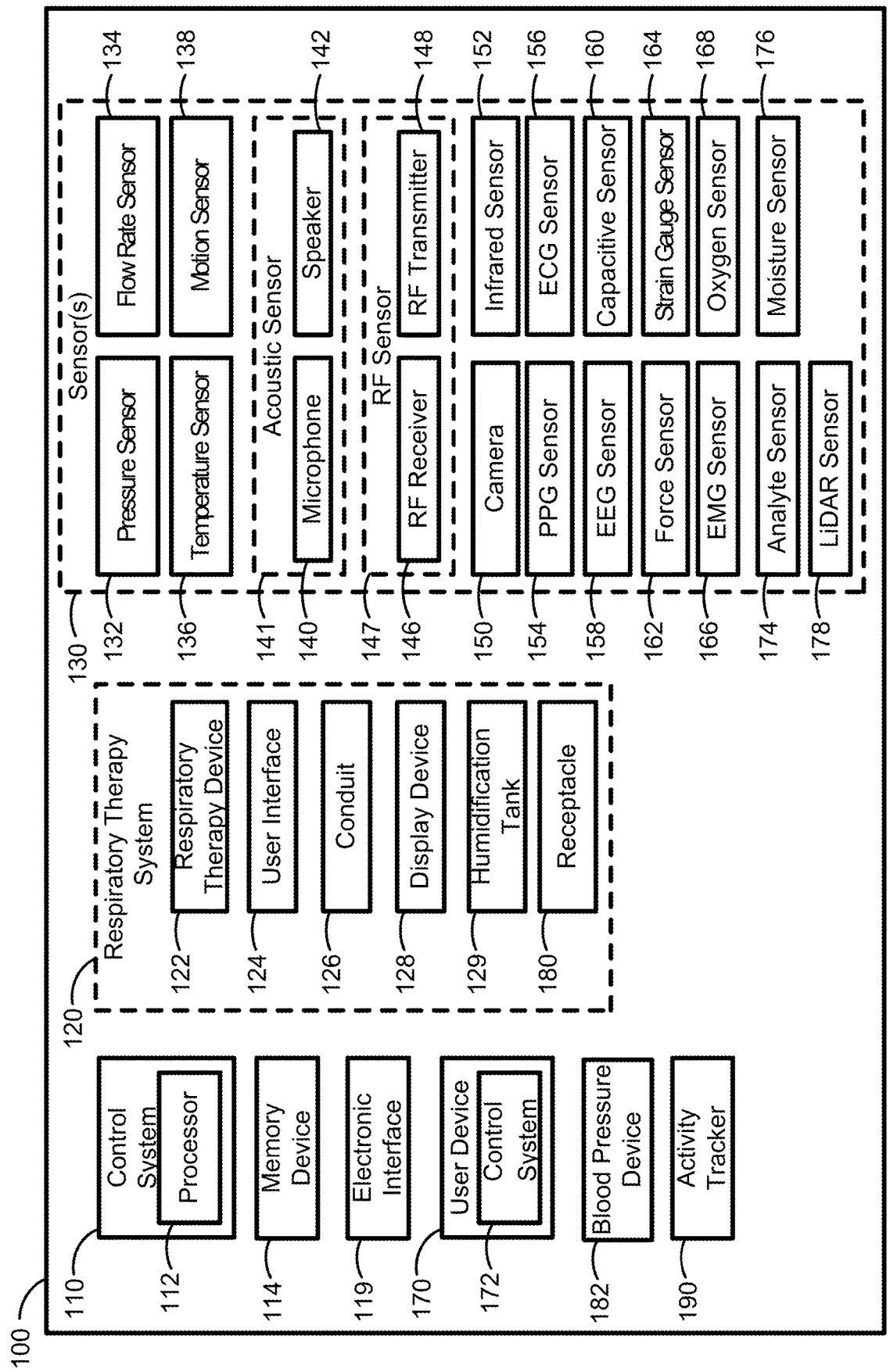
FIG. 1 is a functional block diagram of a system, according to some implementations of the present disclosure.

While the present disclosure is susceptible to various modifications and alternative forms, specific implementations and implementations thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The devices, systems, and methods of the present disclosure solve the above problems by determining sleep status (e.g., sleep state and/or sleep stage) based on parameters associated with modalities other than flow, or based on parameters associated with other modalities in combination with parameters based on flow. The devices, systems, and methods of the present disclosure further solve or ameliorate the above problems by determining an AHI after disregarding false SDB events that occur while a user is not asleep. Accordingly, the false SDB events detected while the user is awake do not incorrectly impact the AHI.

As discussed above, flow-based sleep staging involves calculating parameters related to flow, including respiration rate, respiratory rate variability (over short and longer timescales), and normalized respiratory rate variability. To make up for the shortcomings of flow-based sleep staging, the devices, systems, and methods of the present disclosure can include additional processing based, at least in part, on parameters generated and/or calculated by the respiratory device or other devices within the environment of the user. For example, the respiratory device and/or another smart device in the environment can detect cardiogenic oscillations of the user in order to estimate heart rate and heart rate variability. Parameters that indicate, for example, rapid fluctuations in the signal quality of the cardiogenic oscillatory signal parameters, alone or in combination with changes in the general flow signal parameters, can be used to infer movement of a user. Therefore, heart rate variability (short term heart rate variability, and long term trend analysis over the night) can be further input parameters for determining sleep status.

Additionally, or in the alternative, the devices, systems, and methods can provide a multi-modal ability that combines flow parameters with audio parameters representative of the sleep status of the user. In one or more implementations, the devices, systems, and methods use a microphone within a respiratory device, in the interface or in the tubing, alone or in combination with the flow signal for sleep status determination. The microphone can detect parameters associated with movement events of the user. The parameters can indicate duration, frequency, and intensity of the movement events, for aiding in the determination of the sleep status.

In one or more specific implementations, the movements change the echo reflection of sound in the tube, which can subsequently be detected. Like heart rate, when a user is sleeping, the respiration rate is more steady and slower when asleep than when awake. The rate is even lower when in deep sleep. The addition of movement detection assists in the determination of sleep status because if the flow resulting from respiration rate is more erratic, and there is movement, it is more likely that the user is awake. However, for REM sleep, the flow signal may still be more erratic, although there may be less movement than during awake. The addition of movement detection will further aid in the detection of sleep status, which can focus the calculation of AHI to actual SDB events when the user is asleep, and not count false SDB events that might look like AHI events but that are when the user is awake.

In one or more implementations, AHI can be calculated more granularly than a single AHI. For example, in one or more implementations, AHI can be calculated for multiple sleep sessions, a single sleep session, an hour during a sleep session, or a shorter increment of time. Thus, a user can have a single AHI value stored, reported, and/or used for controlling a respiratory device, or the user can have multiple AHI values stored, reported, and/or used for controlling a respiratory device, among various other potential actions.

In one or more implementations, a user can have AHI determined at a more granular level with respect to sleep stage. For example, the detected sleep stages can be REM and non-REM. In which case, an AHI can be calculated for REM, and a separate AHI can be calculated for non-REM. This can occur in addition to calculating an overall AHI, or without calculating an overall AHI. In one or more implementations, AHI can be calculated for each sleep stage of, for example, N1, N2, N3, and/or REM. This can provide insights into the best sleep stage for a user in terms of getting quality sleep without having an SDB event occur. Alternatively, AHI can be calculated for only N3 and REM, or only N2, N3, and REM.

Referring to FIG. 1, a functional block diagram is illustrated of a system 100 for inferring sleep states and stages, according to aspects of the present disclosure. The system 100 includes a control system 110, a memory device 114, an electronic interface 119, a respiratory therapy system 120, one or more sensors 130, and one or more user devices 170. In some implementations, the system 100 further optionally includes a blood pressure device 182, an activity tracker 190, or any combination thereof.

During use, the respiratory therapy system 120 may detect and count SDB events (e.g., apnea or hypopnea events) during a session of the respiratory therapy system 120 attempting to maintain a medically prescribed air pressure during sleep. From these SDB events, the respiratory therapy system 120 can estimate an AHI. The AHI can be used to stratify SDB risk, and monitor severity across sessions. However, as discussed above, the respiratory therapy system 120 may detect conditions that appear to be apnea or hypopnea events but the user may be awake or in a stage of light sleep (e.g., N1). In which case, there may be a desire to not consider the events detected during an "awake" state, which appear to be an apnea or hypopnea event in the calculation of the AHI. Alternatively, the respiratory therapy system 120 may detect the effects of periodic limb movements (PLMs), and estimate incorrectly that the user is wake. In which case, the respiratory therapy system 120 may miss SDB events that should be considered in the AHI. For example, the person may still be asleep during the PLMs but may have reduced quality sleep. The respiratory therapy system 120 is configured with the ability to more accurately determine the sleep state (e.g., awake or asleep) of a user (e.g., user 210 in FIG. 2), along with the ability to more accurately determine the sleep stage (e.g., N1, N2, N3, REM) of the user, during a session of applying the pressurized air. This ability to more accurately determine the sleep state and sleep stage allows for the respiratory therapy system 120 to more accurately determine the AHI, which can provide better future sessions of preventing the airway from narrowing or collapsing, among other benefits.

The control system 110 includes one or more processors 112 (hereinafter, processor 112). The control system 110 is generally used to control the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, the activity tracker 190, and/or within a housing of one or more of the sensors 130. The control system 110 can be centralized (within one such housing) or decentralized (within two or more of such housings that are physically distinct). In such implementations including two or more housings containing the control system 110, such housings can be located proximately and/or remotely from each other.

The control system 110 can perform the methodologies disclosed herein for the determination of sleep status/stage and calculation of the AHI in "real time" or as a post-process; that is, after the completion of a sleep session. For post-processing implementations, the data used in the methodologies can be stored as a time series of samples at a predefined sampling rate on the memory device 114.

The memory device 114 stores machine-readable instructions that are executable by the processor 112 of the control system 110, and specifically for determining the sleep state/ stage of a user, along with the other methodologies disclosed herein. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory device 122, within a housing of the user device 170, the activity tracker 190, within a housing of one or more of the sensors 130, or any combination thereof. Like the control system 110, the memory device 114 can be centralized (within one such housing) or decentralized (within two or more of such housings that are physically distinct).

In one or more implementations, the memory device 114 can include stored processor control instructions for signal processing, such as sound signal processing, movement signal processing, and the like. Such specific signal processing can include measurement filtering, Fourier transforms, logarithm, position determination, extent determination, difference determination, etc. In one or more implementations, the processor control instructions and data for controlling the disclosed methodologies can be contained in the memory device 114 as software for use by the control system 110 to be considered specific-purpose processors, according to any of the methodologies discussed herein.

In some implementations, the memory device 114 stores a user profile associated with the user, which can be implemented as parameters for inferring states and stages. The user profile can include, for example, demographic information associated with the user, biometric information associated with the user, medical information associated with the user, self-reported user feedback, sleep parameters associated with the user (e.g., sleep-related parameters recorded from one or more sleep sessions), or any combination thereof. The demographic information can include, for example, information indicative of an age of the user, a gender of the user, a race of the user, an ethnicity of the user, a geographic location of the user, a travel history of the user, a relationship status, a status of whether the user has one or more pets, a status of whether the user has a family, a family history of health conditions, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The medical information data can include results from one or more of a polysomnography (PSG) test, a CPAP titration, or a home sleep test (HST), respiratory therapy system settings from one or more sleep sessions, sleep related respiratory events from one or more sleep sessions, or any combination thereof. The self-reported user feedback can include information indicative of a self-reported subjective therapy score (e.g., poor, average, excellent), a self-reported subjective stress level of the user, a self-reported subjective fatigue level of the user, a self-reported subjective health status of the user, a recent life event experienced by the user, or any combination thereof. The user profile information can be updated at any time, such as daily (e.g. between sleep sessions), weekly, monthly, or yearly. In some implementations, the memory device 114 stores media content that can be displayed on the display device 128 and/or the display device 172, discussed below.

The electronic interface 119 is configured to receive data (e.g., physiological data, flow rate data, pressure data, motion data, acoustic data, etc.) from the one or more sensors 130 such that the data can be stored in the memory device 114 and/or analyzed by the processor 112 of the control system 110. The received data, such as physiological data, flow rate data, pressure data, motion data, acoustic data, etc., may be used to determine and/or calculate parameters for inferring sleep states and stages. The electronic interface 119 can communicate with the one or more sensors 130 using a wired connection or a wireless connection (e.g., using an RF communication protocol, a Wi-Fi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver (e.g., an RF transceiver), or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated with the control system 110 and/or the memory device 114 in a housing.

The respiratory therapy system 120 can include a respiratory pressure therapy (RPT) device 122 (referred to herein as respiratory device 122), a user interface 124, a conduit 126 (also referred to as a tube or an air circuit), a display device 128, a humidification tank 129, a receptacle 180 or any combination thereof. In some implementations, the control system 110, the memory device 114, the display device 128, one or more of the sensors 130, and the humidification tank 129 are part of the respiratory device 122.

Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cmH$_2$O, at least about 10 cmH$_2$O, at least about 20 cmH$_2$O, between about 6 cmH$_2$O and about 10 cmH$_2$O, between about 7 cmH$_2$O and about 12 cmH$_2$O, etc. The respiratory device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Generally, the user interface 124 engages the user's face such that the pressurized air is delivered to the user's airway via the user's mouth, the user's nose, or both the user's mouth and nose. Together, the respiratory device 122, the user interface 124, and the conduit 126 form an air pathway fluidly coupled with an airway of the user.

Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cmH$_2$O relative to ambient pressure. For other forms of therapy, such as the delivery of oxygen, the user interface may not include a seal sufficient to facilitate delivery to the airways of a supply of gas at a positive pressure of about 10 cmH$_2$O.

Figure 2:
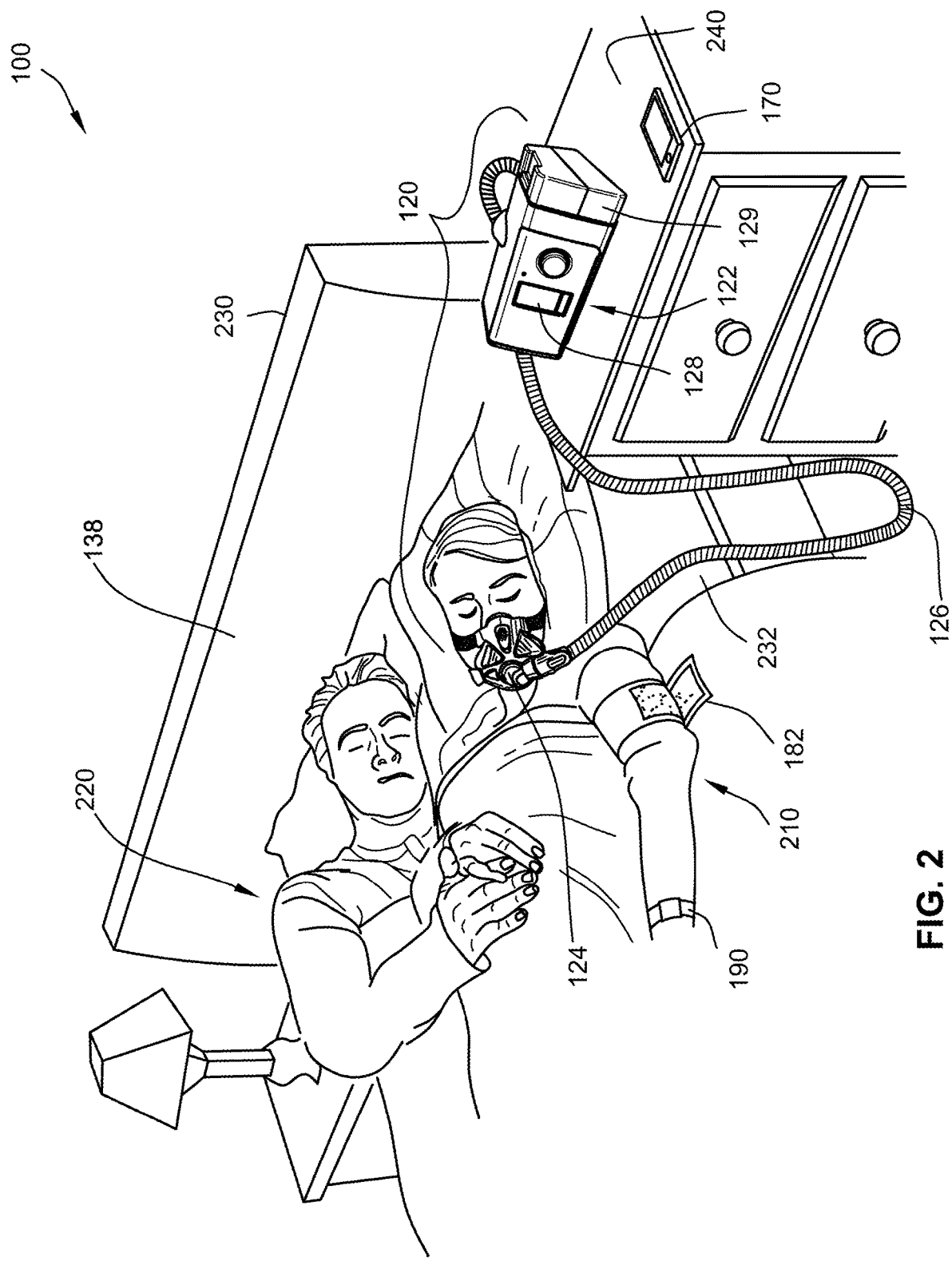
FIG. 2 is a perspective view of at least a portion of the system of FIG. 1, a user wearing a full face mask, and a bed partner, according to some implementations of the present disclosure.

As shown in FIG. 2, in some implementations, the user interface 124 is or includes a facial mask (e.g., a full face mask) that covers the nose and mouth of the user. Alternatively, in some implementations, the user interface 124 is a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 includes a mouthpiece (e.g., a night guard mouthpiece molded to conform to the user's teeth, a mandibular repositioning device, etc.).

The conduit 126 (also referred to as an air circuit or tube) allows the flow of air between two components of the respiratory therapy system 120, such as the respiratory device 122 and the user interface 124. In some implementations, there can be separate limbs of the conduit for inhalation and exhalation. In other implementations, a single limb conduit is used for both inhalation and exhalation.

One or more of the respiratory device 122, the user interface 124, the conduit 126, the display device 128, and the humidification tank 129 can contain one or more sensors (e.g., a pressure sensor, a flow rate sensor, a humidity sensor, a temperature sensor, or more generally any of the sensors 130 described herein). These one or more sensors can be used, for example, to measure the air pressure and/or flow rate of pressurized air supplied by the respiratory device 122.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.) and/or other information (e.g., a sleep score and/or a therapy score (also referred to as a myAir™ score, such as described in WO 2016/061629, which is hereby incorporated by reference herein in its entirety), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122. The humidification tank 129 includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself. In other implementations, the respiratory device 122 or the conduit 126 can include a waterless humidifier. The waterless humidifier can incorporate sensors that interface with other sensor positioned elsewhere in system 100.

In some implementations, the system 100 can be used to deliver at least a portion of a substance from a receptacle 180 to the air pathway the user based at least in part on the physiological data, the sleep-related parameters, other data or information, or any combination thereof. Generally, modifying the delivery of the portion of the substance into the air pathway can include (i) initiating the delivery of the substance into the air pathway, (ii) ending the delivery of the portion of the substance into the air pathway, (iii) modifying an amount of the substance delivered into the air pathway, (iv) modifying a temporal characteristic of the delivery of the portion of the substance into the air pathway, (v) modifying a quantitative characteristic of the delivery of the portion of the substance into the air pathway, (vi) modifying any parameter associated with the delivery of the substance into the air pathway, or (vii) any combination of (i)-(vi).

Modifying the temporal characteristic of the delivery of the portion of the substance into the air pathway can include changing the rate at which the substance is delivered, starting and/or finishing at different times, continuing for different time periods, changing the time distribution or characteristics of the delivery, changing the amount distribution independently of the time distribution, etc. The independent time and amount variation ensures that, apart from varying the frequency of the release of the substance, one can vary the amount of substance released each time. In this manner, a number of different combination of release frequencies and release amounts (e.g., higher frequency but lower release amount, higher frequency and higher amount, lower frequency and higher amount, lower frequency and lower amount, etc.) can be achieved. Other modifications to the delivery of the portion of the substance into the air pathway can also be utilized.

The respiratory therapy system 120 can be used, for example, as a ventilator or a positive airway pressure (PAP) system such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. A motion sensor 138, a blood pressure device 182, and an activity tracker 190 are shown, although any one or more sensors 130 can be used to generate parameters for determining the sleep status and stage of the user 210 during a therapy, sleeping, and/or resting session of the user 210.

The user interface 124 is a facial mask (e.g., a full face mask) that covers the nose and mouth of the user 210. Alternatively, the user interface 124 can be a nasal mask that provides air to the nose of the user 210 or a nasal pillow mask that delivers air directly to the nostrils of the user 210. The user interface 124 can include a plurality of straps (e.g., including hook and loop fasteners) for positioning and/or stabilizing the interface on a portion of the user 210 (e.g., the face) and a conformal cushion (e.g., silicone, plastic, foam, etc.) that aids in providing an air-tight seal between the user interface 124 and the user 210. The user interface 124 can also include one or more vents for permitting the escape of carbon dioxide and other gases exhaled by the user 210. In other implementations, the user interface 124 is a mouthpiece (e.g., a night guard mouthpiece molded to conform to the user's teeth, a mandibular repositioning device, etc.) for directing pressurized air into the mouth of the user 210.

The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

Generally, a user who is prescribed usage of the respiratory therapy system 120 will tend to experience higher quality sleep and less fatigue during the day after using the respiratory therapy system 120 during the sleep compared to not using the respiratory therapy system 120 (especially when the user suffers from sleep apnea or other sleep related disorders). For example, the user 210 may suffer from obstructive sleep apnea and rely on the user interface 124 (e.g., a full face mask) to deliver pressurized air from the respiratory device 122 via conduit 126. The respiratory device 122 can be a continuous positive airway pressure (CPAP) machine used to increase air pressure in the throat of the user 210 to prevent the airway from closing and/or narrowing during sleep. For someone with sleep apnea, their airway can narrow or collapse during sleep, reducing oxygen intake, and forcing them to wake up and/or otherwise disrupt their sleep. The respiratory device 122 prevents the airway from narrowing or collapsing, thus minimizing the occurrences where the user 210 wakes up or is otherwise disturbed due to reduction in oxygen intake.

Referring to back to FIG. 1, the one or more sensors 130 of the system 100 include a pressure sensor 132, a flow rate sensor 134, temperature sensor 136, a motion sensor 138, a microphone 140, a speaker 142, an RF receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, and a Light Detection and Ranging (LiDAR) sensor 178. In one or more implementations, the one or more sensors 130 can include various other sensors, such as an electrodermal sensor, an accelerometer, an electrooculography (EOG) sensor, a light sensor, a humidity sensor, an air quality sensor, or any combination thereof. Generally, each of the one or more sensors 130 are configured to output sensor data that is received and stored in the memory device 114 or one or more other memory devices for, at least in part, achieving the methods disclosed herein.

The one or more sensors 130 are used to detect parameters associated with a user. The parameters can be associated with the flow of pressurized air to the user. The parameters can be associated with various movements of the user, such as body movement, respiration, cardiac movement etc. The parameters can be associated with movement specific to cardiac movement (e.g., heart beats), or specific to other cardiac functions. The parameters can be associated with audio parameters, such as for indicating gross body movements, movements with respect to the heart (e.g., heart beats), movements with respect to the components of the respiratory device 122, characteristics of the user interface 124 and/or conduit 126 of the respiratory therapy system 120, etc. In one or more implementations, the sensors 130 can be part of the respiratory therapy system 120, or the respiratory therapy system 120 can instead communicate with one or more external devices for receiving one or more parameters from the one or more sensors 130 of the external devices, or a combination of both situations, as further discussed below.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the Light Detection and Ranging (LiDAR) sensor 178, more generally, the one or more sensors 130 can include any combination and any number of each of the sensors described and/or shown herein.

Data from one or more sensors 130 that are room environment sensors can be used as parameters as discussed herein, such as temperature throughout a sleep session (e.g., too warm, too cold), humidity (e.g., too high, too low), pollution levels (e.g., an amount and/or concentration of $CO_2$ and/or particulates being under or over a threshold), light levels (e.g., too bright, not using blackout blinds, too much blue light before falling asleep), and sound levels (e.g., above a threshold, types of sources, linked to interruptions in sleep, snoring of a partner). These can be captured by the one or more sensors 130 on a respiratory device 122, on a user device 170, such as smartphone (e.g., connected via Bluetooth or internet), or other devices/systems, such as connected to or part of a home automation system. An air quality sensor can also detect other types of pollution in the room than cause allergies, such as from pets, dust mites, and so forth—and where the room could benefit from air filtration in order to increase use comfort of the user.

Parameters from the user's health (physical and/or mental) condition can also be incorporated. For example, parameters can also relate to health (such as a change due to the onset or offset of illness such as respiratory issue, and/or due to a change in an underlying condition such as a co-morbid chronic condition).

For example, PPG data from the PPG sensor 154 (such as on the mask, headgear, as a patch, as a watch, a ring, or in the ear) could be used to estimate heart rate, blood pressure, and $SpO_2$. The blood oxygenation level could be referenced to the PAP therapy to confirm that no unexpected drops are seen—and also if/when the therapy is off (such as mask removed) to monitor any residual respiratory (e.g. apnea) events. These PPG data can be used to estimate likely daytime headache, and/or suggest a change to PAP therapy, such as further treating flow limitations in addition to pure obstructive events. These PPG data can also be used to check for an inflammation response. Headaches could also be due to a pressure setting that is too high, and might benefit from a reduced pressure, or change to an EPR setting.

Referring back to FIG. 1, as described herein, the system 100 generally can be used to generate data (e.g., physiological data, flow rate data, pressure data, motion data, acoustic data, etc.) associated with a user (user 210 in FIG. 2) of the respiratory therapy system 120 during a sleep session. The generated data can be analyzed to generate one or more sleep-related parameters, which can include any data, reading, measurement, etc. related to the user during the sleep session. The one or more sleep-related parameters that can be determined for the user 210 during the sleep session include, for example, an AHI score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory device 122, a heart rate, a heart rate variability, movement of the user 210, temperature, EEG activity, EMG activity, arousal, snoring, choking, coughing, whistling, wheezing, or any combination thereof.

The one or more sensors 130 can be used to generate, for example, physiological data, flow rate data, pressure data, motion data, acoustic data, etc. In some implementations, the data generated by one or more of the sensors 130 can be used by the control system 110 to determine the duration of sleep and sleep quality of user 210, which is a parameter. For example, a sleep-wake signal associated with the user 210 during the sleep session and one or more sleep-related parameters. The sleep-wake signal can be indicative of one or more sleep states, including sleep, wakefulness, relaxed wakefulness, micro-awakenings, or distinct sleep stages such as a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more of the sensors, such as sensors 130, are described in, for example, WO 2014/047110, US 2014/0088373, WO 2017/132726, WO 2019/122413, and WO 2019/122414, each of which is hereby incorporated by reference herein in its entirety.

The sleep-wake signal can also be timestamped to determine a time that the user enters the bed, a time that the user exits the bed, a time that the user attempts to fall asleep, etc. The sleep-wake signal can be measured by the one or more sensors 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory device 122, or any combination thereof during the sleep session.

The event(s) can include snoring, apneas, central apneas, obstructive apneas, mixed apneas, hypopneas, a mouth leak, a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, or any combination thereof. In some implementations, mouth leak can include continuous mouth leak, or valve-like mouth leak (i.e. varying over the breath duration) where the lips of a user, typically using a nasal/nasal pillows mask, pop open on expiration. Mouth leak can lead to dryness of the mouth, bad breath, and is sometimes colloquially referred to as "sandpaper mouth."

The one or more sleep-related parameters that can be determined for the user during the sleep session based on the sleep-wake signal include, for example, sleep quality metrics such as a total time in bed, a total sleep time, a sleep onset latency, a wake-after-sleep-onset parameter, a sleep efficiency, a fragmentation index, or any combination thereof.

The data generated by the one or more sensors 130 (e.g., physiological data, flow rate data, pressure data, motion data, acoustic data, etc.) can also be used to determine a respiration signal associated with a user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration ratio, a number of events per hour, a pattern of events, pressure settings of the respiratory device 122, or any combination thereof. The event(s) can include snoring, apneas, central apneas, obstructive apneas, mixed apneas, hypopneas, a mouth leak, a mask leak (e.g., from the user interface 124), a restless leg, a sleeping disorder, choking, an increased heart rate, labored breathing, an asthma attack, an epileptic episode, a seizure, or any combination thereof.

Generally, the sleep session includes any point in time after the user 210 has laid or sat down in the bed 230 (or another area or object on which they intend to sleep), and/or has turned on the respiratory device 122 and/or donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session is generally defined as ending once the user 210 removes the user interface 124, turns off the respiratory device 122, and/or gets out of bed 230. In some implementations, the sleep session can include additional periods of time, or can be limited to only some of the above-disclosed time periods. For example, the sleep session can be defined to encompass a period of time beginning when the respiratory device 122 begins supplying the pressurized air to the airway or the user 210, ending when the respiratory device 122 stops supplying the pressurized air to the airway of the user 210, and including some or all of the time points in between, when the user 210 is asleep or awake.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory device 122, the user interface 124, or the conduit 126. The pressure sensor 132 can be used to determine an air pressure in the respiratory device 122, an air pressure in the conduit 126, an air pressure in the user interface 124, or any combination thereof. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of a user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The flow rate sensor 134 can be used to generate flow rate data associated with the user 210 (FIG. 2) of the respiratory device 122 during the sleep session. Examples of flow rate sensors (such as, for example, the flow rate sensor 134) are described in WO 2012/012835, which is hereby incorporated by reference herein in its entirety. In some implementations, the flow rate sensor 134 is configured to measure a vent flow (e.g., intentional "leak"), an unintentional leak (e.g., mouth leak and/or mask leak), a patient flow (e.g., air into and/or out of lungs), or any combination thereof. In some implementations, the flow rate data can be analyzed to determine cardiogenic oscillations of the user.

The temperature sensor 136 outputs temperature data that can be stored in the memory device 114 and/or analyzed by the processor 112 of the control system 110. In some implementations, the temperature sensor 136 generates temperature data indicative of a core body temperature of the user 210 (FIG. 2), a skin temperature of the user 210, a temperature of the air flowing from the respiratory device 122 and/or through the conduit 126, a temperature of the air in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user 210 during the sleep session, and/or detect movement of any of the components of the respiratory therapy system 120, such as the respiratory device 122, the user interface 124, or the conduit 126. The motion sensor 138 can include one or more inertial sensors, such as accelerometers, gyroscopes, and magnetometers. In some implementations, the motion sensor 138 alternatively or additionally generates one or more signals representing bodily movement of the user, from which may be obtained a signal representing a sleep state or sleep stage of the user; for example, via a respiratory movement of the user. In some implementations, the motion data from the motion sensor 138 can be used in conjunction with additional data from another sensor 130 to determine the sleep state or sleep stage of the user. In some implementations, the motion data can be used to determine a location, a body position, and/or a change in body position of the user.

The motion sensor 138 can detect movement of the user. In some implementations, the motion sensor 138 cooperates with the camera 150 (e.g., infrared camera) to determine changes and/or shifts in body temperature with respect to ambient temperature to determine whether a user is moving. In some implementations, the motion sensor 138 utilizes electromagnetic sensing in the infrared wavelength for detecting motion. The use of an IR sensor allows a determination that body temperature slightly falls, to be used as an indication that the user is sleeping. When body temperature rises above a certain level based on infrared sensing, the motion sensor 138 may determine that the user is waking up and/or moving. The temperature change may also be obtained from a temperature sensor attached to the mask of the respiratory system, such that to be in contact with the user's skin, during use of the mask. Other examples of the motion sensor 138 include passive infrared sensors, sensors that emit acoustic signals (as described above and below) and determine whether detected reception of reflected acoustic signals indicate a changing pattern, inertial measurement unit (IMUs), gyroscopes and accelerometers, passive microphones, radio frequency (RF) based sensors, ultra wide band sensors, and so on.

The microphone 140 outputs sound data that can be stored in the memory device 114 and/or analyzed by the processor 112 of the control system 110. The microphone 140 can be used to record sound(s) during a sleep session (e.g., sounds from the user 210) to determine (e.g., using the control system 110) one or more sleep related parameters, which may include one or more events (e.g., respiratory events), as described in further detail herein. The microphone 140 can be coupled to or integrated in the respiratory device 122, the user interface 124, the conduit 126, or the user device 170. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The speaker 142 outputs sound waves. In one or more implementations, the sound waves can be audible to a user of the system 100 (e.g., the user 210 of FIG. 2) or inaudible to the user of the system (e.g., ultrasonic sound waves). The speaker 142 can be used, for example, as an alarm clock or to play an alert or message to the user 210 (e.g., in response to an identified body position and/or a change in body position). In some implementations, the speaker 142 can be used to communicate the audio data generated by the microphone 140 to the user. The speaker 142 can be coupled to or integrated in the respiratory device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g. a SONAR sensor), as described in, for example, WO 2018/050913 and WO 2020/104465, each of which is hereby incorporated by reference herein in its entirety. In such implementations, the speaker 142 generates or emits sound waves at a predetermined interval and/or frequency and the microphone 140 detects the reflections of the emitted sound waves from the speaker 142. In one or more implementations, the sound waves generated or emitted by the speaker 142 can have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters (e.g., an identified body position and/or a change in body position) described in herein such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory device 122, or any combination thereof. In this context, a sonar sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO2018/050913 and WO 2020/104465 mentioned above.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location and/or a body position of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g. a RADAR sensor). In some such implementations, the RF sensor 147 includes a control circuit. The specific format of the RF communication could be Wi-Fi, Bluetooth, or etc.

In some implementations, the RF sensor 147 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or any combination thereof) that can be stored in the memory device 114. The image data from the camera 150 can be used by the control system 110 to determine one or more of the sleep-related parameters described herein. The image data from the camera 150 can be used by the control system 110 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 150 can be used to identify a location and/or a body position of the user, to determine chest movement of the user 210, to determine air flow of the mouth and/or nose of the user 210, to determine a time when the user 210 enters the bed 230, and to determine a time when the user 210 exits the bed 230. The camera 150 can also be used to track eye movements, pupil dilation (if one or both of the user 210's eyes are open), blink rate, or any changes during REM sleep.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 180 nm and about 740 nm.

The PPG sensor 154 outputs physiological data associated with the user 210 (FIG. 2) that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state or sleep stage of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the user 210's breath. In some implementations, the analyte sensor 174 is positioned near the user 210's mouth to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the user 210's nose to detect analytes in breath exhaled through the user's nose. In still other implementations, the analyte sensor 174 can be positioned near the user 210's mouth when the user interface 124 is a nasal mask or a nasal pillow mask. In some implementations, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the user 210's mouth or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be positioned in the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 210, for example, the air inside the user 210's bedroom. The moisture sensor 176 can also be used to track the user 210's biometric response to environmental changes.

One or more Light Detection and Ranging (LiDAR) sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, an orientation sensor, a rain sensor, a soil moisture sensor, a water flow sensor, an alcohol sensor, or any combination thereof.

While shown separately in FIGS. 1 and 2, any combination of the one or more sensors 130 can be integrated in and/or coupled to any one or more of the components of the system 100, including the respiratory device 122, the user interface 124, the conduit 126, the humidification tank 129, the control system 110, the user device 170, or any combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, at least one of the one or more sensors 130 is not physically and/or communicatively coupled to the respiratory device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, a sleep stage, an apnea-hypopnea index (AHI), or any combination thereof. The one or more events can include snoring, apneas, central apneas, obstructive apneas, mixed apneas, hypopneas, an intentional mask leak, an unintentional mask leak, a mouth leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Non-physiological parameters can also include operational parameters of the respiratory therapy system, including flow rate, pressure, humidity of the pressurized air, speed of motor, etc. Other types of physiological and non-physiological parameters can also be determined, either from the data from the one or more sensors 130, or from other types of data.

The user device 170 includes a display device 172. The user device 170 can be, for example, a mobile device such as a smart phone, a tablet, a gaming console, a smart watch, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

The blood pressure device 182 is generally used to aid in generating physiological data for determining one or more blood pressure measurements associated with a user. The blood pressure device 182 can include at least one of the one or more sensors 130 to measure, for example, a systolic blood pressure component and/or a diastolic blood pressure component.

In some implementations, the blood pressure device 182 is a sphygmomanometer including an inflatable cuff that can be worn by a user and a pressure sensor (e.g., the pressure sensor 132 described herein). For example, as shown in the example of FIG. 2, the blood pressure device 182 can be worn on an upper arm of the user 210. In such implementations where the blood pressure device 182 is a sphygmomanometer, the blood pressure device 182 also includes a pump (e.g., a manually operated bulb) for inflating the cuff. In some implementations, the blood pressure device 182 is coupled to the respiratory device 122 of the respiratory therapy system 120, which in turn delivers pressurized air to inflate the cuff. More generally, the blood pressure device 182 can be communicatively coupled with, and/or physically integrated in (e.g., within a housing), the control system 110, the memory device 114, the respiratory therapy system 120, the user device 170, and/or the activity tracker 190.

The activity tracker 190 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation level ($SpO_2$), electrodermal activity (also known as skin conductance or galvanic skin response), a position of the user, a posture of the user, or any combination thereof. The activity tracker 190 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 190 is a wearable device that can be worn by the user, such as a smartwatch, a wristband, a ring, or a patch. For example, referring to FIG. 2, the activity tracker 190 is worn on a wrist of the user 210. The activity tracker 190 can also be coupled to or integrated a garment or clothing that is worn by the user. Alternatively still, the activity tracker 190 can also be coupled to or integrated in (e.g., within the same housing) the user device 170. More generally, the activity tracker 190 can be communicatively coupled with, or physically integrated in (e.g., within a housing), the control system 110, the memory device 114, the respiratory therapy system 120, and/or the user device 170, and/or the blood pressure device 182.

While the control system 110 and the memory device 114 are described and shown in FIG. 1 as being a separate and distinct component of the system 100, in some implementations, the control system 110 and/or the memory device 114 are integrated in the user device 170 and/or the respiratory device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for analyzing data associated with a user's use of the respiratory therapy system 120, according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, the user device 170, and the blood pressure device 182 and/or activity tracker 190. As yet another example, a third alternative system includes the control system 110, the memory device 114, the respiratory therapy system 120, at least one of the one or more sensors 130, activity tracker 190 and the user device 170. As a further example, a fourth alternative system includes the control system 110, the memory device 114, the respiratory therapy system 120, at least one of the one or more sensors 130, the user device 170, and the blood pressure device 182 and/or activity tracker 190. Thus, various systems can be formed using any portion or portions of the components shown and described herein and/or in combination with one or more other components.

Referring again to FIG. 2, the system 100 includes a number of optional components, that are not necessarily required for the operation of the system 100 (i.e., a large number of sensors, a camera etc.). Usually any of these sensors, if able to detect one of the modalities described below, will be sufficient for the system to operate as described here. Having more than one sensor in the system allows parallel and/or independent estimation of the sleep status, which brings improved certainty in the calculated outcome. Using one or more of the indicated sensors, the system determines sleep status, which can include the sleep state of awake or asleep, in addition to the sleep stage (e.g., N1, N2, N3, REM) if asleep. The determination can be based on a modality other than flow, but can also be based on flow in combination with another one or more modalities, such as movement, audio, cardiac, etc. To simplify discussion, the singular form will be used for all components identified in FIG. 3 when appropriate. However, the use of the singular does not limit the discussion to only one of each such component.

As described above, in one or more implementations, the respiratory system 100 can further include, or be associated with, a user device 170. The user device 170 can have the same functionality as the respiratory device 122, with respect to having a control system 172. Moreover, the user device 170 can be various devices, such as a smart home device, a smart phone, a smart watch, a smart speaker, a TV, a smart mask, a smart ring, a fitness tracker, a computing device (e.g., personal computer, laptop, tablet, etc.), a smart pendant, a smart garment, or any other device that has smart functionality by having at least the control system 172, in addition to having the ability to communicate with one or more of the sensors 130 discussed herein, if one or more sensors 130 are not already integrated into the user device 170. A smart device is an electronic device able to connect to other devices or networks, which usually has some processing power that allows it to operate, at least to some extent, interactively and autonomously, in general. Because the user device 170 is used to measure parameters of a user, the user device 170 is broadly associated with the user. In some cases, the user device 170 may be coupled to the user. Such a coupling is being in mechanical contact with the user, either directly, such as in contact with the user's skin, or indirectly through, for example, clothing. Coupled smart devices can include a smart watch, a smart phone, an activity tracker, a smart mask, a smart garment, a smart mattress, a smart pillow, smart sheets, a smart ring, or a wearable health monitor. Non-contact (non-coupled) smart devices may include smart TVs, smart speakers, smart cars, entertainment systems (including vehicle entertainment systems), etc.

The user device 170 may also include and/or be in communication with one or more remote (with respect to the user and the local smart device) servers. These can be arranged to process and store, or just store, data associated with the user. In some cases, these servers, which are usually capable of more complicated and/or intensive computational tasks, may be arranged to receive data from the local smart device, and perform any more computationally demanding tasks. After that the server/s may store and/or return the results back to the local smart device.

In one or more implementations, the control system 110 can perform the methodologies disclosed herein to determine the sleep status of the user, i.e., based on the respiratory flow data obtained by the device flow sensor. The control system 110 of the may be further arranged to collect data from any additional disclosed sensors. Alternatively, the methodologies disclosed herein to determine the sleep status of the user can be implemented by the control system 172 of the user device 170 that is configured to communicate with the respiratory device 122. In such forms, the respiratory device 122 may send one or more signals to the user device 170 representing information that the respiratory device 122 collects and/or generates, and that the user device 170 uses to perform the methodologies.

In one or more alternative implementations, the methodologies disclosed herein to determine the sleep status of the user may be implemented partly by the control system 110 and partly by the control system 172 of the user device 170. For example, the control system 110 can process information to determine the sleep status of a user based on one or more flow parameters. Additionally, the user device 170 can process information, using one or more additional sensors, to determine the sleep status of a user based on one or more other parameters, such as parameters related to body movement of the user, cardiac data of the user, etc. One of the respiratory device 122 and the user device 170 can send the determined sleep status of the user to the other of the respiratory device 122 and the user device 170 for subsequent determination of the final sleep status of the user and additional processing, such as determination of the AHI.

Figure 3:
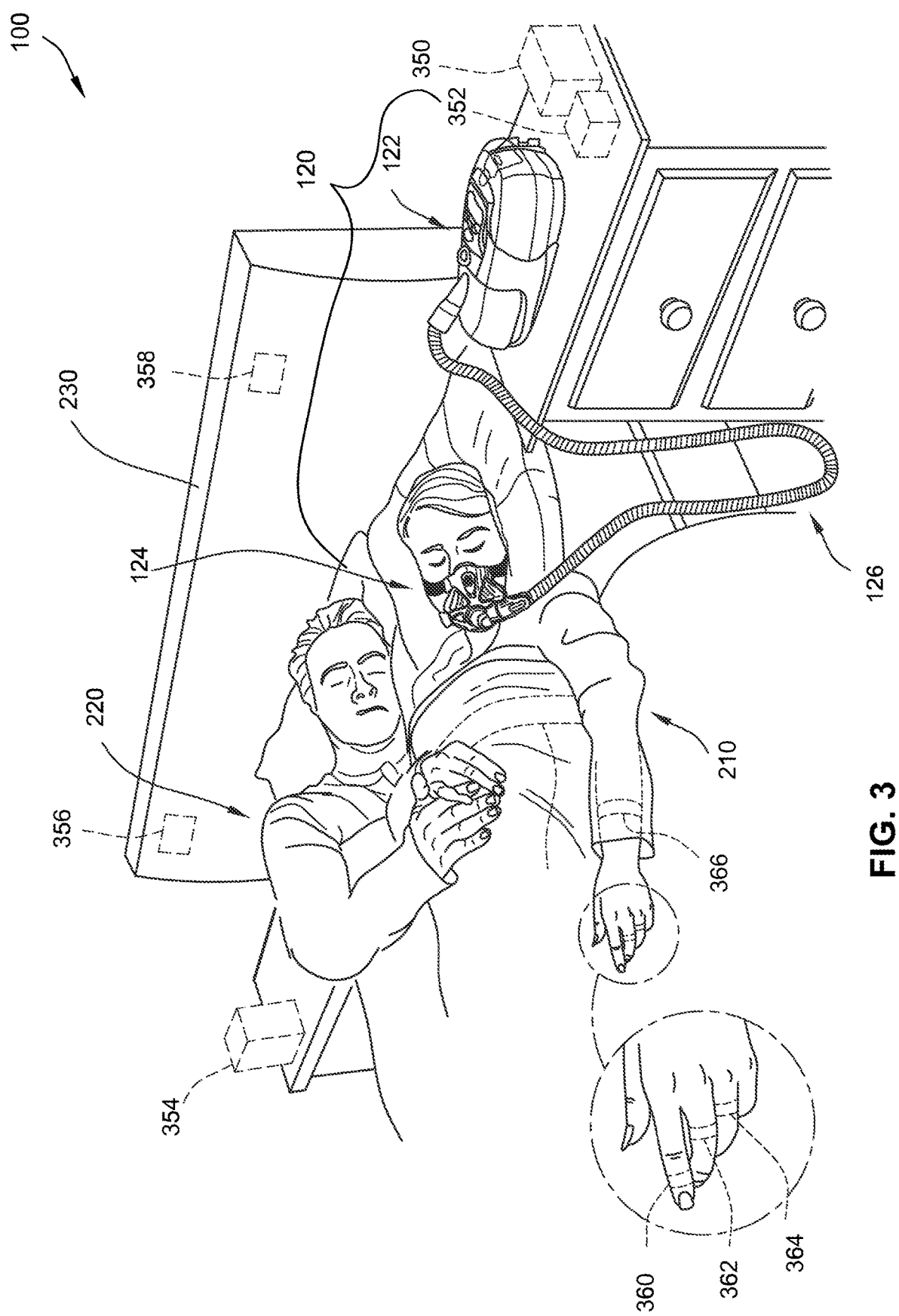
FIG. 3 is another perspective view of at least another portion of the system of FIG. 1, the user wearing a full face mask, and the bed partner, according to some implementations of the present disclosure.

Referring to FIG. 3, another example of the placement of the components of the system 100 in an environment is shown, according to some aspects of the present disclosure. The environment is a bedroom setting that includes again a user 210 and a bed partner 220. The user 210 is wearing a user interface 124 connected via the conduit 126 to the respiratory device 122. The respiratory device 122 includes a flow sensor that can facilitate the measurement of the user 210 respiratory flow. Statistical analysis of the respiratory flow can then be used to calculate sleep parameters, indicating whether the user 210 is awake or asleep, and in what sleep stage the user 210 is at for different points of time, as for example disclosed in International Patent Application Publication No. WO 2014/047110 (PCT/US2013/060652), entitled "SYSTEM AND METHOD FOR DETERMINING SLEEP STAGE," and International Patent Application Publication No. WO 2015/006164 (PCT/US2014/045814), entitled "METHOD AND SYSTEM FOR SLEEP MANAGEMENT"; the contents of both of these applications are hereby incorporated by reference herein in their entireties.

As described in International Patent Application Publication No. WO 2014/047110, whether a person is asleep or awake can be determined without further having to a determine sleep stage, or without first determining a specific sleep stage. In other words, the present disclosure contemplates the determination of a user 210 being awake or asleep, i.e., sleep state, independent of a sleep stage determination, or at least without needing to determine a sleep stage.

In one or more implementations, one or more features can be generated from various data associated with the user 210 with respect to use of the respiratory device and/or the environment of the user 210. The features can be used to determine if the user 210 is awake or asleep. For example, flow data including (but not limited to or requiring) flow and audio or other acoustic signals can be processed to generate respiratory features while the user 210 is using the respiratory device. These respiratory features can be associated with a user 210 that is awake or asleep. Based on the respiratory features being input into a classifier, the classifier can analyze the respiratory features to determine whether the user 210 awake or asleep.

In one or more implementations, the classifier can be trained by inputting previous respiratory or cardiac features (or other features associated with sleep in general) associated with known sleep states of awake or asleep to train the classifier for further sleep state determination. After training, the classifier can be used to determine the sleep state of the user 210. The classifier can be, for example, a linear or quadrant discriminant analysis classifier, decision tree, support vector machine, or a neural network performing a two-state classification, to name just a few examples of such a classifier that can be trained to output a sleep state (e.g., wake/sleep determination) based on inputted features. As a further example, such a classifier may be a rule based processing system that classifies the input features. In some cases, the classifier may include input from a function library for sleep state detection. The library may provide signal processing on one or more sensed signals to estimate movement, activity count, and respiration rates, as examples, on an epoch basis; time, frequency, or time-frequency approaches such as by using wavelet or non-wavelet based processing.

In one or more specific implementations, features associated with the user 210 can be input into a classifier. The classifier may then combine them to produce a number which is then used to estimate the sleep state of awake or asleep. For example, a number may be generated by the classifier and may be a discriminant value. In some implementations, a combination of values within the classifier may be done in a linear fashion. For example, the discriminant value may be a linear weighted combination of the features. The classifier may then generate a suitable Sleep State Label (e.g., asleep, awake, or even present/not present) therefrom. The sleep state classifier thus processes the input features (e.g., wavelet features, breath features, etc.) to detect a sleep state.

Various locations for the components of the system 100 are contemplated. For example, one or more cameras can be mounted in a ceiling of the room. Non-contact sensing can also be achieved with non-contact sensors like cameras, motion sensors, radar sensors, sonar sensors, and/or microphones placed at positions 350, 352, 354, 356, 358. One or more microphones, microphones and speaker combinations for sonar, or transmitters and receivers for radar can be mounted to the bed 230 and/or a wall of the room, etc. In some implementations, having multiple cameras or microphones at different locations in the room allows for multiple video angles and stereo sound which can allow for directly distinguishing and eliminating noise coming from the bed partner 220 relative to the user 210. In some implementations, contact sensors like PPG sensors, GSR sensors, ECG sensors, actigraphy sensors and so on can be placed on the user 210 at locations 360, 362, 364, and 366.

Although the present disclosure is described primarily in the context of detecting the sleep status and/or stage of a user while the user is using a respiratory therapy device, the methodologies of the present disclosure can apply to any SDB devices. For example, the methodologies of the present disclosure can apply to mandibular repositioning devices. Further, the methodologies of the present disclosure can apply to any individual that would like more information about his or her sleep, and not necessarily an individual that suffers from some form of sleep-disordered breathing. The methodologies that do not require a respiratory therapy system can, therefore, be applied to any individual who has the other components described above within the system 100 that can determine the sleep stage and/or stage of the user. In which case, for example, the respiratory therapy system 120 can be omitted from the system 100, and the determination of sleep state and/or sleep stage can be accomplished by the other components of the system 100.

Figure 4:
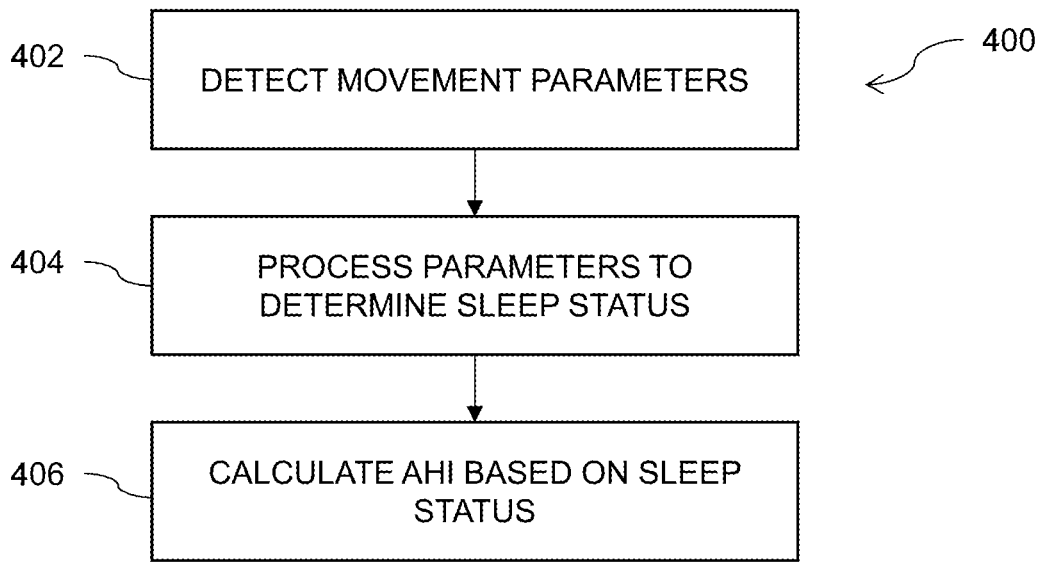
FIG. 4 is a flow diagram of a process for detecting sleep status of a user based on movement of a user, according to aspects of the present disclosure.

FIG. 4 illustrates an example of a process 400 for detecting sleep status based on movement of a user, according to aspects of the present disclosure. For purposes of convenience, the following description will be in reference to the process 400 being performed by the respiratory therapy system 120. However, the process 400 can be performed by the respiratory therapy system 120 and/or a remote external sensor and/or computing device, such as any one of the sensors/devices (local or otherwise) included in the system of FIG. 1.

At step 402, the respiratory therapy system 120 detects one or more parameters with respect to movement of a user during a sleep session. In one or more implementations, the sleep session can optionally include a session of applying pressurized air to an airway of the user. In one or more implementations, the one or more parameters can relate to duration, rate, frequency (or period), intensity or type of movement of the user, as well as to a combination thereof. In one or more implementations, the one or more parameters can be measured based on one or more sensors placed on the user, placed in proximity of the user, or a combination thereof. The sensors acquire at least one parameter that represents the movement of the user, such as the gross body movement of the user, movement of one or more limbs of the user, etc. In one or more implementations, this movement will include any movement not related to respiratory or cardiac functions. Examples of such general body movements, which throughout this description are referred to as bodily or body movement, include, for example, turning over, twitching, adjusting position, limb movement etc. Parameters indicative of these movements could be provided by a radio frequency bio-motion sensor, but could also be acquired by one or more actigraphy-based sensors or pressure sensors embedded in a sensor film or sensor mattress, by a bioimpedance measurement system, an ultrasonic sensor, or an optical sensor, and the like.

In one or more implementations, the movement can include any one or more of respiration movement, cardiac movement, and gross body movement. With respect to respiration movement, the movement parameters can be calculated based on either flow information collected by the respiratory device or on other movement sensors (contact (respiratory belt or other wearable inertial measurement sensor) or not-contact (RF or acoustic) sensors). The respiratory parameters can include respiratory amplitude, relative respiratory amplitude, respiratory rate, and respiratory rate variability.

In one or more implementations, the pressurized air is applied to the airway of the user through a tube and/or a mask connected to a respiratory device, and at least one sensor of the one or more sensors can be on or within the tube, the mask, or a combination thereof. In one or more implementations, the at least one sensor can include an inertial measurement unit on or within the tube, the mask, or a combination thereof. In one or more implementations, at least one sensor of the one or more sensors can include an inertial measurement unit within a smart device coupled to the user. For example, the smart device can include a smart watch, a smart phone, an activity tracker, a smart mask worn by the user during therapy, or a health monitor.

In one or more implementations, parameters associated with bodily movement and/or respiration movement can be obtained through a non-invasive sensor, such as a pressure sensitive mattress or a radio-frequency (RF) motion sensor. The RF motion sensor is a non-contact sensor, as the user does not have to be in mechanical contact with the sensor. The RF motion sensor can be configured to be sensitive to movement within a distance of, for example, 1.2 meters and avoid detecting movement from more distant objects. This can prevent or limit interference from, for example, a second user in the bed or nearby moving objects, such as fans. One or more specific examples of such sensors can be found in International Patent Application Publication No. WO 2007/143535 (PCT/US2007/070196), entitled "APPARATUS, SYSTEM, AND METHOD FOR MONITORING PHYSIOLOGICAL SIGNS"; the contents of which are hereby incorporated by reference herein in their entireties, and International Patent Application Publication No. WO 2015/006164 (PCT/US2014/045814), referenced above.

It will be understood that in some versions of the present technology other sensors, such as those further described herein, may also or alternatively be employed to generate movement (respiration signals) for the detection of sleep stage.

At step 404, the respiratory therapy system 120 processes the one or more parameters to determine a sleep status of the user, the sleep status being one of the user being awake, asleep or being in a specific sleep stage. In one or more implementations, some specific parameters that may be estimated and analyzed relate to the frequency, amplitude, and bursts of higher frequency (faster) movements as a user moves from wakefulness to the twilight stage of sleep stage N1. The combined nature of movement pattern and breathing rate value and waveform shape may be used to classify sleep status.

In one or more implementations, the respiratory therapy system 120 can use a classifier for determining the sleep status of the user. The classifier can be derived from any one or more of supervised machine learning, deep learning, a convolutional neural network, and a recurrent neural network. The classifier can receive the parameters from step 402 as inputs and process the parameters to determine the sleep status. In one or more implementations, the classifier can be a full sleep-staging classifier using a one-dimensional convolutional neural network. In this approach, a set of feature decoders is learned directly from the raw or pre-processed flow signal.

In one or more implementations, the processing of the one or more parameters includes processing a signal representative of at least one parameter of the one or more parameters over time. Thus, over time, the respiratory therapy system 120 may adapt to subject specific data in order to increase the accuracy of this classification (e.g., the typical baseline breathing rate and amount of movement of the subject—i.e., how much the user moves around in bed/fidgets as the user is falling asleep) may be learned and employed in the estimation process.

At step 406, the respiratory therapy system 120 calculates an AHI for the user during the session based, at least in part, on the sleep status, which is based on the user's movement. The AHI is calculated so that one or more events that affect the calculating of the apnea-hypopnea index of the user are disregarded in response to the sleep status being determined as awake during the one or more events. The one or more events can be one or more apneas, one or more hypopneas, or a combination thereof. Thus, when one or more SBD events occur, but the sleep status indicates that the user is awake, the SBD events are disregarded so that the AHI is not affected by the incorrect events.

Figure 5:
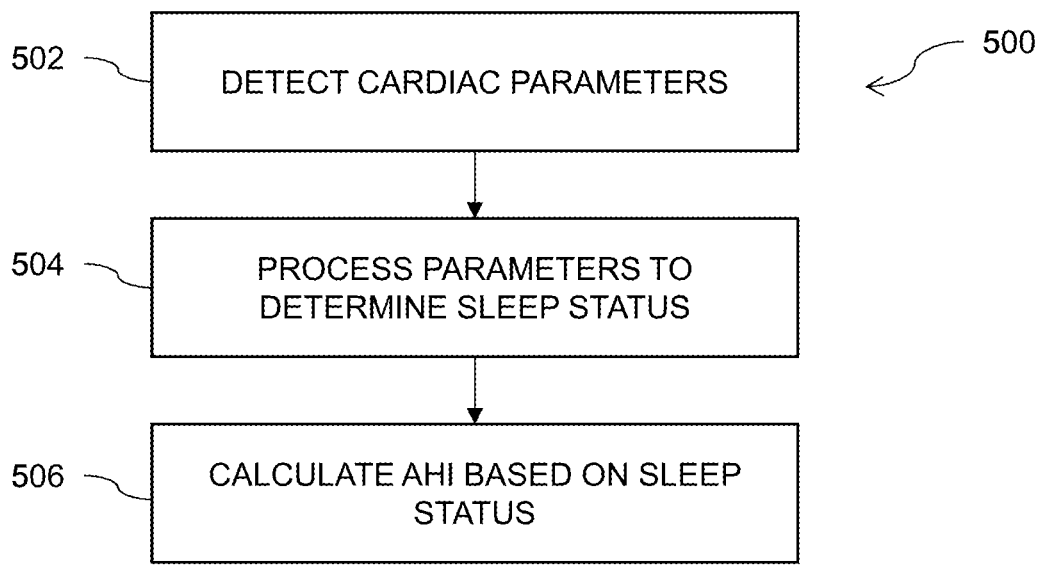
FIG. 5 is a flow diagram of a process for detecting sleep status of a user based on cardiac activity, according to aspects of the present disclosure.

FIG. 5 illustrates an example somewhat similar to that in FIG. 4, but where the process 500 for detecting sleep status is based on cardiac activity, according to aspects of the present disclosure. For purposes of convenience, the following description will be in reference to the process 500 being performed by respiratory therapy system 120. However, the process 500 can be also performed by the respiratory therapy system 120 in conjunction with any one or more of the sensors and devices (local or otherwise) included in the system of FIG. 1.

At step 502, the respiratory therapy system 120 detects one or more parameters with respect to cardiac activity of a user during a sleep session. In one or more implementations, the sleep session can optionally include a session of applying pressurized air to an airway of the user. In one or more implementations, the pressurized air is applied to the airway of the user through a tube and a mask connected to a respiratory device. At least one sensor of the one or more parameters can be on or within the tube, the mask, or a combination thereof.

In one or more implementations, cardiac signal can be extracted from the respiratory flow signal (collected by the flow sensor of the respiratory device or from additional contact or non-contact sensors), or based on the pressure wave created at the surface of the body called a ballistocardiogram. In some cases, due to a combination of positioning, body type, and distance from a sensor, the cardiac signals will provide a signal in which individual pulses can be clearly seen via movement. In such cases, heart beats will be determined by a threshold passing technique. For example, a pulse is associated with the point where the signal exceeds the threshold. In more complex but typical cases, the ballistocardiogram will present a more complex but repeatable pulse shape. Therefore, a pulse shape template can be correlated with the acquired cardiac signal, and places where the correlation is high will be used as the heart beat locations. The pulses can subsequently be measured using movement sensors, such as the above-discussed RF sensors.

More specifically, similar to the implementations discussed above with respect to movement, in one or more implementations, the sensor can be a radio frequency sensor, either separate from or integrated with the respiratory device. The sensor can transmit a radio-frequency signal towards the user. The reflected signal is then received, amplified, and mixed with a portion of the original signal. The output of this mixer can be low-pass filtered. The resulting signal contains information about cardiac activity of the user, usually superimposed on the respiratory signal collected from the user. In an alternative implementation, the sensor may also use quadrature transmission in which two carrier signals 90 degrees out of phase are used. In the limits that the pulse becomes very short in time, such a system can be characterized as an ultrawideband (UWB) radio-frequency sensor.

In one or more implementations, the one or more parameters can relate to heart rate, heart rate variability, cardiac output, or a combination thereof of the user. In one or more implementations, the heart rate variability can be calculated over a period of time of one minute, five minutes, ten minutes, half an hour, an hour, two hours, three hours, or four hours.

At step 504, the respiratory therapy system 120 processes the one or more parameters to determine a sleep status of the user, the sleep status being at least one of awake, asleep or a sleep stage. Similar to above, in one or more implementations, the respiratory system can use a classifier for determining the sleep status of the user. The classifier can be derived from any one or more of supervised machine learning, deep learning, a convolutional neural network, and a recurrent neural network. The classifier can receive the parameters from Step 502 as inputs and process the parameters to determine the sleep status. In one or more implementations, the classifier can be a full sleep-staging classifier using a one-dimensional convolutional neural network. In this approach, a set of feature decoders is learned directly from the raw or pre-processed flow signal.

At step 506, the respiratory therapy system 120 calculates an apnea-hypopnea index for the user during the session based, at least in part, on the sleep status. The AHI is, as in the above described cases, usually calculated on the basis if the respiratory data collected from the flow sensor in the respiratory device. The knowledge of the sleep status of the user allow the AHI index to be calculated so that one or more events that affect the calculating of the apnea-hypopnea index of the user are disregarded in response to the sleep status being determined as awake during the one or more events. The one or more events can be one or more apneas, one or more hypopneas, or a combination thereof. Thus, when one or more SBD events occur but the sleep status determined for that point of time indicates that the user is awake, the SBD events are disregarded so that the AHI is not affected by the incorrectly scored events.

Figure 6:
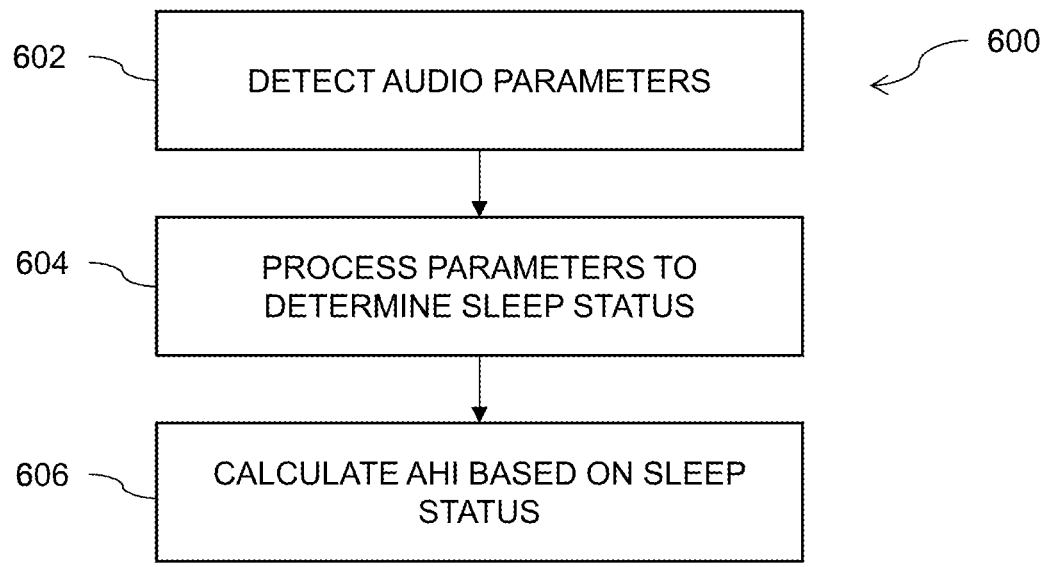
FIG. 6 is a flow diagram of a process for detecting sleep status of a user based on audio parameters associated with the user, according to aspects of the present disclosure.

FIG. 6 illustrates an example of a process 600 for detecting sleep status based on audio parameters associated with a user, according to aspects of the present disclosure. For purposes of convenience, the following description will be in reference to the process 600 being performed by the respiratory therapy system 120. However, the process 600 can be performed by the respiratory therapy system 120 in association with additional sensors and computing devices, such as any one of the sensors/devices (local or otherwise) indicated in the system 100 of FIG. 1.

At step 602, the respiratory therapy system 120 uses an internal (for the respiratory system) on an external microphone to detect one or more parameters with respect to audio associated with a user during a sleep session. In one or more implementations, the sleep session can optionally include a session of applying pressurized air to an airway of the user. The audio parameters can relate to sounds passively heard by, for example, a microphone positioned in proximity to a user. For example, the tubing may generate sounds from dragging across an object, such as a sheet, or running along sideboard.

Alternatively, the audio parameters can relate to sounds emitted and received back via an echo at a microphone positioned in proximity to a user. The sounds can be emitted by a device configured specifically to emit sound, such as a speaker, or by a device that indirectly emits sounds, such as a blower on the respiratory device.

In one or more specific implementations, the audio can be associated with (1) one or more movements of the user, (2) one or more movements of a tube, a mask, or a combination thereof connected to a respiratory device configured to apply the pressurized air to the user, or (3) a combination thereof. For example, the user can move and that movement can make a sound that is picked up by a microphone. Alternatively, the user can move a piece of equipment of the respiratory system, such as the tubing, and that sound of the tubing can be picked up by the microphone. A movement of the tube may indicate activity of the user. Alternatively, a loud snore may indicate that the user is fast asleep.

In one or more implementations, the detecting of the one or more parameters with respect to audio associated with the one or more movements of the tube, the mask, or a combination thereof is based on a cepstrum analysis, a spectral analysis, a fast Fourier transform, or a combination thereof of one or more audio signals. The audio can be detected based on one or more microphones within a tube, a mask, or a device connected to the tube and the device and that provides the pressurized air to the airway of the user.

More specifically, the tubing can act as a waveguide. The change in characteristics of the tubing as it moves as a waveguide change the positions of reflections (e.g., echoes) within the tubing. Mathematical processing of the changes in the reflections, such as through cepstrum processing, wavelet analysis, square signal, or root mean square it, etc. can detect the changes and equate the changes to movement of the user. Further details of the mathematical processing can be found in International Patent Application Publication No. WO 2010/091362 (PCT/AU2010/000140), entitled "ACOUSTIC DETECTION FOR RESPIRATORY TREATMENT APPARATUS," the contents of which are incorporated by reference herein in their entirety. Additional acoustic sensors are disclosed in International Patent Application Publication No. WO 2018/050913 (PCT/EP2017/073613), entitled "APPARATUS, SYSTEM, AND METHOD FOR DETECTING PHYSIOLOGICAL MOVEMENT FROM AUDIO AND MULTIMODAL SIGNALS," International Patent Application Publication No. WO 2019/122412 (PCT/EP2018/086762), entitled "APPARATUS, SYSTEM, AND METHOD FOR HEALTH AND MEDICAL SENSING," International Patent Application Publication No. WO 2019/122413 (PCT/EP2018/086764), entitled "APPARATUS, SYSTEM, AND METHOD FOR MOTION SENSING," and International Patent Application Publication No. WO 2019/122414 (PCT/EP2018/086765), entitled "APPARATUS, SYSTEM, AND METHOD FOR PHYSIOLOGICAL SENSING IN VEHICLES," the contents of which are hereby incorporated by reference in their entireties.

At step 604, the respiratory therapy system 120 processes the one or more parameters to determine a sleep status of the user, the sleep status being at least one of awake, asleep or a sleep stage. Similar to above, in one or more implementations, the respiratory therapy system 120 can use a classifier for determining the sleep status of the user. The classifier can be derived from any one or more of supervised machine learning, deep learning, a convolutional neural network, and a recurrent neural network. The classifier can receive the parameters from Step 602 as inputs and process the parameters to determine the sleep status. In one or more implementations, the classifier can be a full sleep-staging classifier using a one-dimensional convolutional neural network. In this approach, a set of feature decoders is learned directly from the raw or pre-processed flow signal.

At step 606, the respiratory therapy system 120 calculates an apnea-hypopnea index for the user during the session based, at least in part, on the sleep status. The AHI is calculated so that one or more events that affect the calculating of the apnea-hypopnea index of the user are disregarded in response to the sleep status being determined as awake during the one or more events. The one or more events can be one or more apneas, one or more hypopneas, or a combination thereof. Thus, when one or more SBD events occur but the sleep status indicates that the user is awake, the SBD events are disregarded so that the AHI is not affected by the incorrect events.

Figure 7:
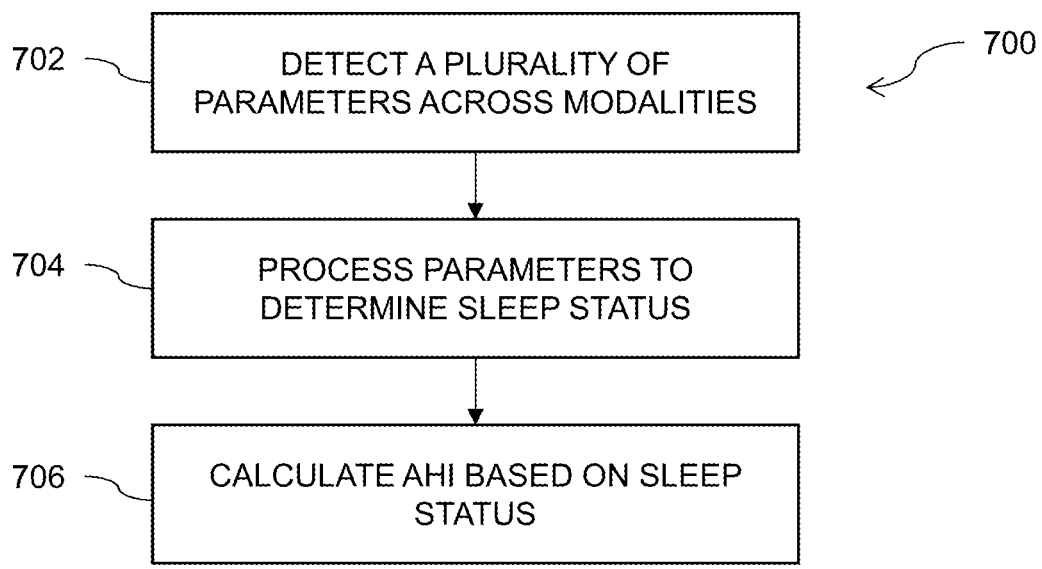
FIG. 7 is a flow diagram of a process for detecting the sleep status of a user based on multiple different modalities, according to aspects of the present disclosure.

FIG. 7 illustrates an example of a process 700 for detecting the sleep status of a user based on multiple different modalities, according to aspects of the present disclosure. For purposes of convenience, the following description will be in reference to the process 700 being performed by the respiratory therapy system 120. However, the process 700 can be performed by the respiratory therapy system 120 in conjunction with any other sensor or device (local or otherwise), included in FIG. 1.

At step 702, the respiratory therapy system 120 detects a plurality of parameters associated with a user during a session of applying pressurized air to an airway of the user. Each parameter of the plurality of parameters is associated at least with one modality, such as movement of the user, flow of the pressurized air, cardiac activity of the user, audio associated with the user, etc. The detection is multi-modal such that the plurality of parameters covers at least two of the modalities. For example, the parameters may include body movement and respiratory flow, cardiac movement and respiratory flow, audio and respiratory flow, etc.

At step 704, the respiratory therapy system 120 processes the plurality of parameters to determine a sleep status of the user, the sleep status being at least one of awake, asleep or a sleep stage. Similar to above, in one or more implementations, the respiratory therapy system 120 can use a classifier for determining the sleep status of the user. The classifier can be derived from any one or more of supervised machine learning, deep learning, a convolutional neural network, and a recurrent neural network. The classifier can receive the parameters from Step 702 as inputs and process the parameters to determine the sleep status. In one or more implementations, the classifier can be a full sleep-staging classifier using a one-dimensional convolutional neural network. In this approach, a set of feature decoders is learned directly from the raw or pre-processed flow signal.

In one or more implementations, parameters of three different modalities are segmented into time epochs, and statistical features are generated for each epoch. For example, these features might be the signal variance, spectral components, or peak values, and these are grouped into vectors Xr, Xn, and Xc. The vectors can then form a single vector X of features. These features are combined to determine the probability that the epoch corresponds to a certain sleep state (e.g., user asleep, user awake). The classification from epochs can be further combined with classification from other epochs to form higher level decisions, such as the sleep stage of the user.

In one or more implementations using an RF sensor with respect to detecting bodily movement, respiratory activity, and cardiac activity, bodily movement can be identified by using zero-crossing or energy envelope detection algorithms (or more complex algorithms), and used to form a "motion on" or "motion off" indicator. The respiratory activity is typically in the range 0.1 to 0.8 Hz, and can be derived by filtering an original signal of the sensor with a band-pass filter whose passband is in that region. The cardiac activity can be detected (i.e. in the respiratory flow signal collected by the respiratory device or by other contact or non-contact sensor) as signals at higher frequencies, which can be accessed by filtering with a bandpass filter with a pass band such as 1 to 10 Hz.

In one or more implementations, the system starts with testing which modalities provide the best quality signal. One or more of these is then used in any further measurements. In an additional implementation, the system may start with two or more predetermined modalities. However, in some cases the processing may determine that the sleep status of the user cannot be determined based on one or more parameters of the plurality of parameters associated with one of the two or more predetermined modalities. For example, one of the predetermined modalities may be respiratory flow. If the respiratory device determines that the sleep state cannot be determined based on flow alone, for the above-discussed deficiencies with respect to flow, thereafter the processing of the one or more parameters of the plurality of parameters can be associated with either the second one of the two predetermined modalities, or on the second one plus an additional (third) modality. For example, the second or the third modality may be one of body movement of the user, cardiac activity of the user, audio associated with the user, etc.

In one or more implementations, the determination that the sleep status of the user cannot be determined can be based on satisfaction of a threshold determination metric. The threshold determination metric can be based on two or more parameters of the plurality of parameters conflicting with respect to sleep state, sleep state, or a combination thereof. In one or more implementations, the two or more conflicting parameters can be from two or more different modalities. In one or more implementations, a conflict between two or more conflicting parameters is resolved by disregarding a parameter derived on a basis of low quality data and/or increased weight is given to a parameter extracted from data of higher quality. Accordingly, each modality and/or parameter can be weighted according to data quality. Sleep status (e.g., sleep state and sleep stage) can be determined from the modality and/or parameter with the higher weighting based on, for example, that modality and/or parameter being traditionally more accurate. Thus, in one or more implementations, processing of the plurality of parameters can be based on a sub-set of the plurality of parameters from a selected two or more modalities of the plurality of modalities. The selected two or more modalities can be selected in accordance with a weighting based on data quality.

The threshold determination metric can be based on a plurality of previous parameters associated with the user during one or more previous sessions of applying pressurized air to the airway of the user. The previous parameters may be verified from previous sessions as accurately reflecting the sleep status of the user. Thereafter, a classifier can be used based on this learned information for providing the threshold determination. The processing is performed by a sleep staging classifier based on one or more of supervised machine learning, deep learning, a convolutional neural network, or a recurrent neural network.

For example, Table 1 lists features—specifically physiological responses of a user—used by a respiratory system in determining sleep stages.

TABLE 1

| Physiological response | Wake | NREM Sleep | REM Sleep | Information contained in flow signal? |
|---|---|---|---|---|
| Respiration rate | ↑ | ↓ | ↗↘↗ | Yes |
| Activity | ↑↑ | ↓ | ↓↓ | Yes. A mic could add additional fidelity |
| Tidal volume | ↑ | ↓ | ↗↘↗ | Approximated based on inspiration/expiration |
| Heart Rate | ↑ | ↓ | ↗↘↗ | Yes, via cardiogenic oscillations. These are not available in all body positions, and signal quality varies from user to user. When available, augment processing |
| Airway resistance | — | ↑ | ↗↘↗ | Inferred through shape of breath (morphological processing) |
| Obstructive apnea | — | ↓ | ↑ | Yes, more likely during REM sleep because of reduced muscle tone in the upper airway that naturally occurs during REM sleep |
| Central apnea | — | ↑ | ↓ | Yes, more likely during Non-REM sleep |
| Snoring (non-apneic) | — | ↑ | ↓ | Yes |
| Snoring (apneic) | — | ↓ | ↑ | Yes |

For Table 1, the listed sleep stages are non-REM sleep and REM sleep, within the context of the sleep state of asleep.

The listed sleep states are awake and asleep. The physiological responses of the user are respiration rate, activity, tidal volume, heart rate, airway resistance, obstructive apnea, central apnea, snoring (non-apneic), and snoring (apneic). Each one of these features can potentially be determined based on flow signals from the respiratory device and subsequently used for determining the sleep stage. However, the determination is based on a likelihood, such as more likely, less likely, and variable. Yet, the combination of an additional modality to the modality of flow for determining sleep state and sleep stage increases the accuracy of the determined state/stage. The increased accuracy leads to better determinations and outcomes, such as a more accurate AHI.

At step 706, the respiratory therapy system 120 calculates an apnea-hypopnea index for the user during the session based, at least in part, on the sleep status. The AHI is calculated so that one or more events that affect the calculating of the apnea-hypopnea index of the user are disregarded in response to the sleep status being determined as awake during the one or more events. The one or more events can be one or more apneas, one or more hypopneas, or a combination thereof. Thus, when one or more SBD events occur but the sleep status indicates that the user is awake, the SBD events are disregarded so that the AHI is not affected by the incorrect events.

Figure 8:
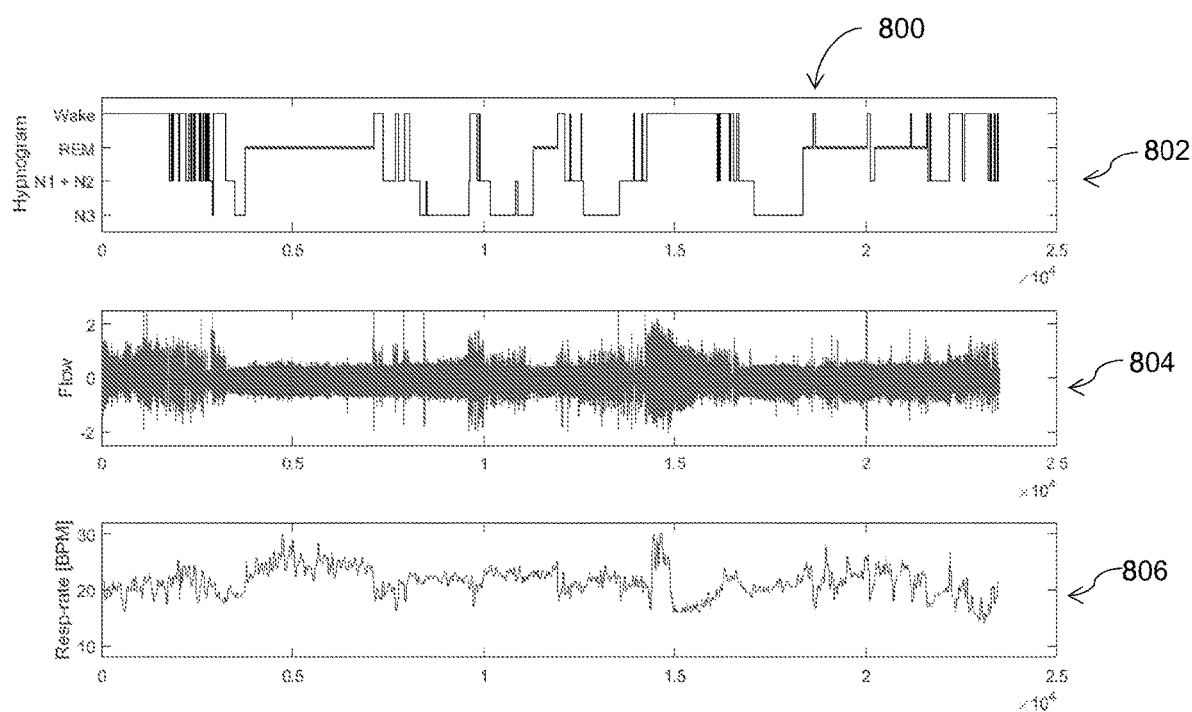
FIG. 8 is a diagram of a sleep hypnogram, according to aspects of the present disclosure.

FIG. 8 shows several graphs associated with a sleep session of a user. These include the respiratory flow diagram 804 and the respiratory rate (in beats per minute) diagram 806. Parameters associated with these diagrams are processed to determine the hypnogram plot 806, which illustrates the sleep state of the user (i.e., wake or non-awake), and the sleep stage if not awake (i.e., N1+N2, N3, and REM). The respiratory rate diagram 806 may be based on data received from the respiratory flow diagram 804. In many respiratory therapy devices, the respiratory flow diagram 804 is plotted and the AHI is calculated based on data obtained by using a flow sensor of the respiratory device. However, the respiratory flow data may also be obtained by independent measurement, such as by way of an additional contact or non-contact sensor, as previously discussed in this text. Accordingly, calculation of AHI may also be performed based on data obtained by these alternative sensors. Furthermore, such additional sensor/s may provide information for other modalities, such as the cardiac or body movement of the user, as well to any audible signals generated by the user during the sleep session. By processing data related to more than one modality, a more accurate hypnogram plot 806 can be generated that accurately reflects the sleep status of the user during a session of being provided pressurized air with a respiratory device. This may result in more accurate calculation of the user AHI.

In one or more implementations, after determining the sleep status, the AHI, or both, within any one or more of the processes described above with respect to FIGS. 4-7, an action can be initiated based, at least in part, on the sleep status, the AHI, or a combination thereof. In one or more implementations, the action can include one or more of (1) saving a record of the apnea-hypopnea index, (b) communicating the apnea-hypopnea index to an external device, displaying information on a screen or (c) adjusting an operational setting of a device. For example, one or more settings of the respiratory device 122 can be adjusted based on the detected sleep state, sleep stage, and/or AHI. In one example, a more accurately detected AHI may indicate an improvement in the user's sleep disorder breathing and may automatically reduce the respiratory pressure setting of the respiratory device 122. This can improve the user comfort without necessarily jeopardizing the therapeutic effect of using the respiratory device 122, possibly also improving the user's compliance with the prescribed treatment. Where the device that detects the sleep state and/or the AHI is not the respiratory device 122, such as the user device 170, the sleep state, the sleep stage, and/or the AHI can be transmitted to the respiratory device 122, or the respiratory therapy system 120. Accordingly, one or more actions can be taken that, for example, make using therapy more compelling by giving richer (e.g., more accurate AHI and/or sleep status) feedback to the user on sleep quality. More accurate sleep-staging also could be used to provide more information back to the user to improve engagement by providing consumer features, and aim to raise patient adherence by providing feedback to the user that quantifies the benefits of therapy.

While the present disclosure has been described with reference to one or more particular implementations or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:
   detecting one or more parameters associated with a user during a sleep session of the user, each parameter of the one or more parameters being associated at least with one modality, and the one or more parameters covering a plurality of modalities, the modalities including movement of a user, flow of pressurized air, cardiac activity of the user, audio associated with the user, or a combination thereof;
   processing the one or more parameters to determine a sleep status of the user, the sleep status being at least one of awake, asleep, or a sleep stage, the processing the one or more parameters including:
      determining that the sleep status of the user cannot be determined based on one or more parameters of the plurality of parameters associated with a first modality of the plurality of modalities; and
      responsive to the sleep status of the user not being determined, processing one or more parameters of the plurality of parameters associated with a second modality of the plurality of modalities to determine the sleep status of the user; and
   calculating an apnea-hypopnea index for the user during the sleep session based, at least in part, on the sleep status.

2. The method of claim 1, wherein one or more events that affect the calculating of the apnea-hypopnea index of the user are disregarded in response to the sleep status being determined as awake during the one or more events.

3. The method of claim 1, wherein, for the one or more parameters that are with respect to movement of the user, the one or more parameters relate to duration, period, rate, frequency, intensity, type of movement of the user, or a combination thereof, and the one or more parameters are measured based on one or more sensors placed on the user, placed in proximity of the user, or a combination thereof.

4. The method of claim 3, wherein at least one sensor of the one or more sensors includes a motion sensor.

5. The method of claim 1, wherein, for the one or more parameters that are with respect to cardiac activity of the user, the one or more parameters relate to heart rate, heart rate variability, cardiac output, or a combination thereof of the user.

6. The method of claim 5, wherein the heart rate variability is calculated over a period of time of one minute, five minutes, ten minutes, half an hour, an hour, two hours, three hours, or four hours.

7. The method of claim 5, wherein the detecting of the one or more parameters is based on a cepstrum analysis, a spectral analysis, a fast Fourier transform, or a combination thereof of one or more flow signals, one or more audio signals, or a combination thereof.

8. The method of claim 1, wherein, for the one or more parameters that are with respect audio associated with the user, the audio is associated with (1) one or more movements of the user, (2) one or more movements of a tube, a mask, or a combination thereof connected to a respiratory device configured to apply pressurized air to the user, or (3) a combination thereof.

9. The method of claim 8, wherein the detecting of the one or more parameters with respect to the audio associated with the one or more movements of the tube, the mask, or a combination thereof is based on a cepstrum analysis, a spectral analysis, a fast Fourier transform, or a combination thereof of one or more flow signals, one or more audio signals, or a combination thereof.

10. The method of claim 1, wherein, for the one or more parameters that are with respect to movement of the user, the method further comprising:
  initiating an action based, at least in part, on the apnea-hypopnea index, the sleep status, or a combination thereof.

11. The method of claim 10, wherein the action includes one or more of (1) saving a record of the apnea-hypopnea index, (b) communicating the apnea-hypopnea index to an external device, or (c) adjusting an operational setting of a device.

12. The method of claim 10, wherein the processing of the one or more parameters includes processing a signal representative of at least one parameter of the one or more parameters over time.

13. The method of claim 1, wherein the determination that the sleep status of the user cannot be determined is based on satisfaction of a threshold determination metric.

14. The method of claim 13, wherein the threshold determination metric is based on two or more parameters of the plurality of parameters conflicting with respect to the determined sleep status, sleep stage, or a combination thereof.

15. A system comprising:
  one or more sensors configured to detect one or more parameters associated with a user during a sleep session of the user, each parameter of the one or more parameters being associated at least with one modality, and the one or more parameters covering a plurality of modalities, the modalities including movement of a user, flow of pressurized air, cardiac activity of the user, audio associated with the user, or a combination thereof;
  memory storing machine-readable instructions; and
  a control system including one or more processors configured to execute the machine-readable instructions to:
    process the one or more parameters to determine a sleep status of the user, the sleep status being at least one of awake, asleep, or a sleep stage, the one or more processors further configured to execute the machine-readable instructions to:
    determine that the sleep status of the user cannot be determined based on one or more parameters of the plurality of parameters associated with a first modality of the plurality of modalities; and
    responsive to the sleep status of the user not being determined, process one or more parameters of the plurality of parameters associated with a second modality of the plurality of modalities to determine the sleep status of the user; and
    calculate an apnea-hypopnea index for the user during the sleep session based, at least in part, on the sleep status.

16. The system of claim 15, wherein one or more events that affect the calculating of the apnea-hypopnea index of the user are disregarded in response to the sleep status being determined as awake during the one or more events.

17. The system of claim 15, wherein, for the one or more parameters that are with respect to movement of the user, the one or more parameters relate to duration, period, rate, frequency, intensity, type of movement of the user, or a combination thereof, and the one or more parameters are measured based on one or more sensors placed on the user, placed in proximity of the user, or a combination thereof.

18. The system of claim 17, wherein at least one sensor of the one or more sensors includes a motion sensor.

19. The system of claim 15, wherein, for the one or more parameters that are with respect to cardiac activity of the user, the one or more parameters relate to heart rate, heart rate variability, cardiac output, or a combination thereof of the user.

20. The system of claim 19, wherein the heart rate variability is calculated over a period of time of one minute, five minutes, ten minutes, half an hour, an hour, two hours, three hours, or four hours.

21. The system of claim 19, wherein the detecting of the one or more parameters is based on a cepstrum analysis, a spectral analysis, a fast Fourier transform, or a combination thereof of one or more flow signals, one or more audio signals, or a combination thereof.

22. The system of claim 15, wherein, for the one or more parameters that are with respect audio associated with the user, the audio is associated with (1) one or more movements of the user, (2) one or more movements of a tube, a mask, or a combination thereof connected to a respiratory device configured to apply pressurized air to the user, or (3) a combination thereof.

23. The system of claim 22, wherein the detecting of the one or more parameters with respect to the audio associated with the one or more movements of the tube, the mask, or a combination thereof is based on a cepstrum analysis, a spectral analysis, a fast Fourier transform, or a combination thereof of one or more flow signals, one or more audio signals, or a combination thereof.

24. The system of claim 15, wherein, for the one or more parameters that are with respect to movement of the user, the control system is further configured to execute the machine-readable instructions to:
  initiate an action based, at least in part, on the apnea-hypopnea index, the sleep status, or a combination thereof.

25. The system of claim 24, wherein the action includes one or more of (1) saving a record of the apnea-hypopnea index, (b) communicating the apnea-hypopnea index to an external device, or (c) adjusting an operational setting of a device.

26. The system of claim 24, wherein the processing of the one or more parameters includes processing a signal representative of at least one parameter of the one or more parameters over time.

27. The system of claim 15, wherein the determination that the sleep status of the user cannot be determined is based on satisfaction of a threshold determination metric.

28. The system of claim 27, wherein the threshold determination metric is based on two or more parameters of the plurality of parameters conflicting with respect to the determined sleep status, sleep stage, or a combination thereof.

* * * * *